US006946070B2

(12) United States Patent
Hammen et al.

(10) Patent No.: US 6,946,070 B2
(45) Date of Patent: Sep. 20, 2005

(54) COMPOSITE MATRICES WITH INTERSTITIAL POLYMER NETWORKS

(76) Inventors: Richard F. Hammen, 4200 Fox Farm Rd., Missoula, MT (US) 59802; John P. Hammen, 4200 Fox Farm Rd., Missoula, MT (US) 59802

(*) Notice: Subject to any disclaimer, the term of this patent is extended or adjusted under 35 U.S.C. 154(b) by 0 days.

(21) Appl. No.: 09/808,732

(22) Filed: Mar. 14, 2001

(65) Prior Publication Data

US 2002/0043499 A1 Apr. 18, 2002

Related U.S. Application Data

(60) Provisional application No. 60/189,313, filed on Mar. 14, 2000.

(51) Int. Cl.$^7$ .............................................. B01D 15/08
(52) U.S. Cl. ................................ 210/198.2; 210/502.1; 210/635; 210/656; 502/402
(58) Field of Search ................................ 210/635, 656, 210/659, 198.2, 502.1; 502/402

(56) References Cited

U.S. PATENT DOCUMENTS

| | | | | |
|---|---|---|---|---|
| 3,808,125 A | * | 4/1974 | Good ....................... | 210/198.2 |
| 3,878,092 A | * | 4/1975 | Fuller ...................... | 210/198.2 |
| 3,954,678 A | * | 5/1976 | Marquisee ............... | 252/62.54 |
| 4,177,038 A | * | 12/1979 | Biebricher et al. ........... | 8/192 |
| 4,824,578 A | | 4/1989 | Schneider et al. .......... | 210/674 |
| 5,135,627 A | * | 8/1992 | Soane ..................... | 204/182.8 |
| 5,334,310 A | * | 8/1994 | Frechet .................... | 210/198.2 |
| 5,653,875 A | * | 8/1997 | Betz et al. ............... | 210/198.2 |
| 5,723,601 A | * | 3/1998 | Larsson ...................... | 536/165 |
| 5,728,457 A | * | 3/1998 | Frechet ...................... | 210/635 |
| 6,136,187 A | * | 10/2000 | Zare ......................... | 210/198.2 |
| 6,210,570 B1 | * | 4/2001 | Holloway ................. | 210/198.2 |
| 6,238,565 B1 | * | 5/2001 | Hatch ......................... | 210/635 |

FOREIGN PATENT DOCUMENTS

| | | | | |
|---|---|---|---|---|
| EP | 0045823 A1 | 2/1982 | .............. | 210/198.2 |
| EP | 0106769 A1 | 4/1984 | .............. | 210/198.2 |
| EP | 0328256 A1 | 8/1989 | .............. | 210/198.2 |
| WO | WO 90/07965 A1 | 7/1990 | .................. | 210/635 |
| WO | WO 94/00237 A1 | 1/1994 | .............. | 210/198.2 |
| WO | WO 99/51316 A1 | 10/1999 | .............. | 210/198.2 |

OTHER PUBLICATIONS

Snyder, Introduction to Modern Liquid Chromatography, 1979, John Wiley & Sons, New York, pp. 276–279.*

* cited by examiner

*Primary Examiner*—Ernest G. Therkorn
(74) *Attorney, Agent, or Firm*—Dorsey & Whitney LLP; Richard F. Trecartin

(57) ABSTRACT

The present invention relates in general to the preparation and use of matrices having solid spaces, interstitial spaces and interstitial polymer networks. In particular, the interstitial polymer networks have utility in chemical and biochemical separations, solid phase synthesis, catalysis of chemical reactions, and immobilized enzyme reactors. The interstitial polymer networks in one embodiment comprise crosslinked polymers suspended in the interstitial spaces from and/or between solid particles. The matrices are characterized by high ligand and functional group density and by reversible high sorptive and binding capacity, and are substantially accompanied by a very low nonspecific adsorption or interaction with molecules such as proteins. Moreover, the matrices of the invention exhibit other characteristics highly desirable in chromatographic and catalytic applications, such as high physical rigidity, high ligand density, chemical stability, high ligand reactivity, and rapid exchange and reaction kinetics.

12 Claims, 11 Drawing Sheets

COMPOSITE MATRICES WITH INTERSTITIAL POLYMER NETWORKS

This application claims the benefit of provisional application 60/189,313, filed Mar. 14, 2000.

FIELD OF THE INVENTION

The present invention relates in general to the preparation and use of matrices having solid space, interstitial space and an interstitial polymer network. The interstitial polymer network in one embodiment comprises a crosslinked polymer within the interstitial spaces.

BACKGROUND OF THE INVENTION

Research, product, and drug development in the chemical and pharmaceutical industries rely heavily upon synthetic chemistry and separation science. Chromatographic separation processes rely upon the differential partitioning of solute molecules between a solid or stationary phase and the mobile phase that is passed through the chromatographic matrix. Individual sample components are separated from each other because each molecule or ion has a different affinity for the stationary phase. Components that have a low affinity for the stationary phase will migrate faster through a chromatographic matrix than those components that have a high affinity for the stationary phase. In some cases the affinity between solute components and the stationary phase is so great that there may be no migration at all of the component through a matrix that has a significant concentration of binding sites available. The differential affinities of sample components to the stationary phase lead to differential rates of migration through the column. Each component exits the column at a different time and this time differential can be exploited for analytical purposes or for purposes of collecting the purified components. The separation efficiency is determined by the amount of spreading of the respective solute bands as they pass through the chromatographic matrix.

In hypothetical analyses of separations in a chromatographic column, those knowledgeable in the field consider a plurality of connected and hypothetical zones or theoretical plates that contain mobile phase, stationary phase and component solutes in concentrations that vary in time and in space as a chromatographic separation occurs. The number of theoretical plates in a chromatographic column is calculated from its actual performance with a component molecule. The number of theoretical plates for a component molecule is proportional to the affinity of the stationary phase for the analyte divided by the width of the peak of the component band emerging from the column. It is of great importance in the field of chemical separations to have columns with large numbers of theoretical plates, and columns with efficiencies exceeding 100,000 plates per meter are becoming readily available to enable workers to perform difficult separations. It is also of great importance to reduce the time required for chromatographic separations. Unfortunately, the rate of equilibrations that occur between the stationary phase and solute molecules are severely limited by the nature of existing chromatographic matrices, and band spreading and loss of resolution occur if separations are attempted at high flow velocity. This problem forces workers in the field to make a difficult choice between the time costs of slow analyses and the performance costs of decreased resolution.

SUMMARY OF THE INVENTION

The invention includes a matrix comprising solid space, interstitial space and an interstitial polymer network. The solid space in one embodiment is solid particles which are in physical contact with each other. The interstitial space is the space that is between the surfaces of the solid particles. The interstitial space comprises the interstitial polymer network.

The interstitial polymer network "IPN" in one embodiment is attached to the solid space. When particles are used, the IPN is attached to at least one of the solid particles. It is preferred that the attachment comprise a covalent linkage. In some embodiments, the IPN is attached to the solid particles via an intermediate molecule referred to as a tether molecule. In such situations, the tether molecule is preferably attached covalently to the surface of the solid particle and comprises a polymerizable unit, generally a monomer unit, that can integrate into the interstitial polymer network during in situ polymerization.

In other embodiments, the IPN is attached to at least two of the solid particles and forms an integrated contiguous network of polymers spanning the particles. The matrix in such embodiments comprises solid particles which are substantially bonded to each other. Such matrices are characterized as being capable of independently maintaining their clinical structure.

In a preferred embodiment, the IPN is crosslinked. Such cross-linked polymer networks generally comprises crosslinking members having a length of between 10 to 1000 angstroms which link linear and/or branched polymeric chains. The length and number of cross-linking molecules and the distance between them theoretically defines the pore size of the IPN.

The IPN is effectively a large pore polymer contained within the interstitial space of the matrix. While not being bound by theory, it is believed that the IPN has properties of both a solid and a solute in solution. For example, the IPN generally is immobile, being bound to a solid surface. Yet, the IPN acts as if it is a solute. The IPN provides minimal flow resistance to solutions passing through the matrix via the interstitial spaces. In addition, the interstitial polymer network provides enhanced kinetic interaction between the polymer network and solutes contained in a solution. The combination of these two properties allows for the high throughput of solutions through the matrix without substantial loss of kinetic reactivity with solutes contained therein.

For example, in some embodiments, the interstitial polymer network may comprise a first member of a binding pair. When contacted with a solution containing a second member of the binding pair, a high throughput system is generated wherein high linear velocities of a solution containing the second binding member can be passed through the matrix while maintaining a high retention rate for the second binding member.

In other embodiments, the interstitial polymer network comprises a reactive moiety such as an enzyme, chemical catalyst and chemical reagents useful for chemical synthesis, e.g., nucleic acid or protein synthesis as well as other forms of combinatorial chemistry. In such embodiments, the reactants such as substrates and the like may be passed through the matrix so as to allow a contact with the immobilized reactive moiety in the IPN.

The matrix of the invention is made in one embodiment by contacting a plurality of solid particles in a container. The particles contact each other in a regular or irregular way to form interstitial spaces between the surfaces of the particles. An interstitial polymer network is then formed in the interstitial spaces generally by polymerizing molecular units capable of forming linear and/or branched polymers. Such polymerization can be alone or in combination with polyfunctional cross-linking molecules. In some embodiments, additional polymerizable molecules are incorporated into the copolymerization reaction which comprise a functional group. The functional group is chosen so that after the IPN is formed various other molecules can be added to the polymer network via the functional group.

In some embodiments, it is preferred that a tether molecule be used to link the interstitial polymer network to the solid support. When tether molecules are used, they form a part of the IPN. In this regard, tether molecules preferably are covalently linked to the solid support and comprise a polymerizable unit which can be used to participate in the in situ polymerization. The tether molecule is preferably added to the particles before the particles are combined.

In other embodiments, blocking molecules are attached to the solid particles to reduce non-specific binding which may otherwise be associated with the ultimate use contemplated for the matrix. In this regard, as with the tether molecules, it is preferred that such blocking molecules be added prior to combining the particles.

The above described matrix can be used in many applications and can take many forms depending upon the use of the matrix. The matrix can be formed within a separation device such as a chromatographic column or microchannel in a microfluidic device. Such separation devices can be used in combination with an apparatus adapted for use with a variety of other separation devices, such a microtiter plates, and planar arrays on a porous membrane or filter support. Preferred channel dimensions in microfluidic devices are from 5–100 microns diameter. The substances separated by the separation devices that are used in combination with the composites of the present invention can include proteins, nucleic acids, antibodies, pharmaceutical products, and the like. The rapid sorption-desorption kinetics of the composites of the present invention allow high throughput screening separations to be carried out.

DETAILED DESCRIPTION OF THE INVENTION

Figure 1:
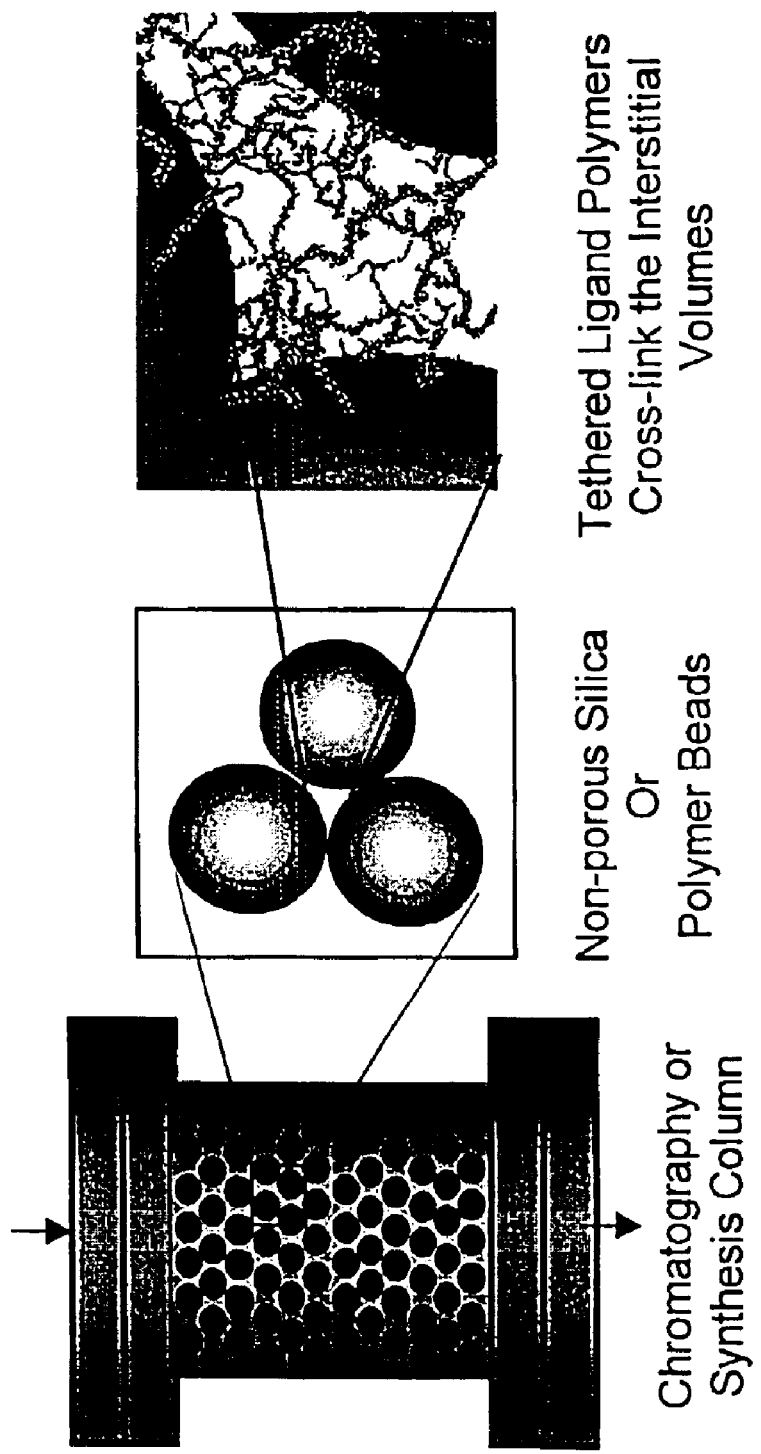
FIG. 1 is a conceptual diagram of a composite matrix with an interstitial polymer network. The right panel of the Figure shows a model of the polymer network in the interstitial spaces between the spheres.

The present invention relates to composite materials. The composite materials sometimes referred to as a matrix comprise solid materials or an assemblage of solid particles (both sometimes referred to as solid supports) having surfaces that define interstitial space within the solid material or assemblage of particles. The interstitial space contains an IPN that occupies at least part of the interstitial spaces and permits the flow and exchange of liquids, solutes, and gases through the IPN and among the matrix of solid materials.

The solid support materials used in forming the matrix includes any substance which is insoluble in the fluids passing through the matrices and that maintains its dimensional integrity while fluids flow through the composite matrix. The solid material can have a wide variety of sizes and shapes which will determine the general size and shape of the solid space and interstitial space in the matrix.

In the case of solid particles, they may comprise substances such as metals, metal oxides, resins, or glasses. The function of the solid particles is to provide a matrix defining the interstitial spaces and to provide a structure which contains the IPN. An aspect of the present invention is the rapid flux of fluids and solutions through the matrix, and accordingly it is a requirement of the solid particles that they maintain their structural integrity under the conditions of fluid flow through the matrix. The solid particles preferably also have a surface to which polymers can be bound, preferably by means of covalent bonds. A preferred solid support is a polymer resin possessing surface chemical functionalities that react with polymeric reagents during a polymerization process that creates the IPN, thereby grafting the polymer chains of the IPN to the solid surface. Preferred solid particles are not porous.

The shape of the solid support can be spherical or irregular beads, fibers, membranes, frits, membranes or frits in microtiter plates and solid phase extraction cartridges, capillaries in solid membranes and frits, and capillary columns.

Synthetic resin particles include, without limitation, such materials as polystyrene, polysulfone, polyethersulfone, polyolefins (e.g., polyethylene and polypropylene), polyacrylates, polyvinyl acetate (and partially hydrolyzed versions thereof), ring-opening polymers, polyethers, epoxide polymers, polyesters, polyamides, phenol-formaldehyde polymers, heterocyclic polymers, polysiloxanes, polyphosphazenes, and the like. The preferred resin supports are composed of resins that have structural rigidity. The most preferred resin supports are highly crosslinked polyacrylates and polystyrenes that are made by methods known to those skilled in the art of resin preparation.

Particularly preferred solid supports include metal oxide (including but not limited to titanium oxide, zirconium oxide, chromium oxide, and iron oxide) and any other similar ceramic material including silicon nitride and aluminum nitride. The preferred mineral oxide supports of the present invention include silica, zirconium oxide, and titanium oxide. The most preferred mineral oxide solid is silica.

Another aspect of the solid support is that it may be composed of a material that can be chemically modified with a "tether molecule" to enable bonding to the polymer network. An example of an advantageous and preferred solid support is a polystyrene resin that can be derivatized or modified by chemistries known by those of usual skill. The most preferred solid support with a surface that can be chemically modified with a tether molecule is silica.

The solid supports comprise particles, including irregularly or spherically shaped particles, fibers, cylinders, or masses of material that have interior surfaces and thereby have interstitial spaces among and between the surfaces when the particles are assembled into a matrix. The solid materials can be selected by for the advantageous properties of cost and the flow characteristics of composite matrices made with the particles. A remarkable characteristic of the present invention is the variety of shapes and forms that the composites can be made in.

Some applications of the invention use low cost solid supports. Exemplary materials are quartz sand, beach sand, fiberglass, hollow or solid silica microspheres, and the like. When the particles are assembled into the matrix of the invention, the size and shape of the particles will determine the dimensions of the interstitial spaces between and among the solid support particles. The dimensions of the interstitial spaces are determined by the solid packing characteristics of the particles. It is most preferable to assemble the solid support particles into a matrix, so that the solid matrix is dimensionally stable and the matrix will not shift or deform under the pressure of fluid flow through the matrix. A preferred and exemplary technique known to skilled artisans is to pack particles into a column, using high flow and pressure, vibration, and combinations of the same to create a stable and well packed bed. Another preferred assemblage of the particles is in the form of a thin array of particles. A preferred assembly, if fiber particles are used, is the form of a filter paper or membrane disc.

In another aspect of the invention, the solid support can comprise a continuous mass of material, such a porous monolith or a porous frit material. Monolithic chromatography columns have been prepared from both metal oxide and organic polymer substances. The methods for monolith manufacture are known to those skilled in the art. The interior surfaces of the monoliths can be covered with a wide variety of chemical functional groups, ion exchange moieties, ligands, and so forth. The methods for surface functionalization of the internal pores of monolith columns is also well known. For purposes of the invention, the convective through pores define the interstitial space of the monolith. Monolith columns and structures are characterized by the permeability of the structures to fluid flow. The permeability is an approximate function of the average diameter of the pores by which convective flow of solutions through the monoliths occurs. Preferred pore diameters of the monoliths are 10–100 nanometers. More preferred average pore diameters are in highly permeable monoliths, with pore diameters ranging from 1.0 micrometers to 1000 micrometers. The most preferred average pore diameters are from 100–1000 nanometers.

It can be readily appreciated that capillary tubes and microchannels in microfluidic devices are also an advantageous solid supports for making interstitial spaces. Capillary columns are used in many diameters and lengths for chromatography and are readily available. As used in the invention, preferred capillary or channel diameters are 5–20 microns. More preferred capillary diameters are 60–200 microns. The most preferred diameters are 20–60 microns. When a single capillary is used, the IPN in the capillary is preferably cross linked. The capillary tubes or microchannels may be of any length that is appropriate to the application. It can be readily seen that the capillary tubes can also be packed in bundles, with the interior of the capillary forming part of the interstitial space and the exterior of the capillary tubes between the outside walls of the capillaries will comprise another part of the interstitial space.

The solid materials can be assembled into matrices of any shape or size. The matrix may be in the shape of a column of particles that are assembled in a tubular cylinder. It can be appreciated that the interstitial space could have a dimension along the axis of a column that is many centimeters to a few meters in length. Without being bound by theory, it is believed that the interstitial polymer network relies upon multiple point covalent attachment to the solid support to maintain its structural rigidity when fluids flow through it.

It can be appreciated that the interstitial spaces in the solid support matrix can be found in a number of shapes, sizes, and geometries. The interstitial space between arrays of solid support particles of in the interior of porous monolith or frit materials are highly irregular and can be made up and a wide range of the interstitial spaces. The size of the interstitial spaces between arrays of particles is a function of the particle shapes and the average particle diameters. In order for the IPN to be substantively occupy a useful portion of the interstitial spaces and remain stable to fluid flow through the matrix, the polymer mass of the IPN is preferably connected by at least two, and preferably multiple bonds to the solid support matrix. Preferably, small interstitial distances across the interstitial spaces are spanned by the IPN. On the other hand, small interstitial spaces reduce the permeability of the solid support relative to those matrices with larger interstitial distances. Large interstitial spaces will, in contrast, make composites with higher permeability, but will also require the macromolecules of the IPN be of higher molecular weight to cross the interstitial spaces and be bound to more than one point on the solid support. The preferred dimensions of the interstitial spaces can be defined by the distance between any point in the interstitial space and the nearest solid support surface. By way of example, if there is a point in the interstitial space that is 10 micrometers from the nearest solid support surface, then it is desirable that the IPN be of a molecular weight and size that is at least 10 micrometers in length, so it can extend from the support to the center of that interstitial space. While it is difficult to know the exact distances from points in the interstitial spaces to the support surfaces, it is simple to define a composite matrix by the size and shape of particles that is can be constructed with. For some applications it is useful to use particles with average diameters of 1–10 microns. Preferred particle sizes for the solid support are from 40–1000 microns. The most preferred average particle sizes for the solid support are from 10–40 microns.

For embodiments of the present invention in which the interstitial space is wholly or partially cylindrical in shape, such as a tube, a capillary, or a pore in a monolithic support material, preferred diameters of the interstitial spaces are 5–15 microns and from 200–1000 microns. The most preferred diameters are from 15–200 microns. For embodiments in which the interstitial space is comprised of the void volumes between particles packed in a matrix, the irregular geometry of the interstitial spaces only allows approximate definitions of the size of the interstitial spaces. Preferred maximum distances between adjacent particles in the matrix are from 1–1000 microns. More preferred interstitial distances are between 2–200 microns, while the most preferred interstitial distances are between 3–50 microns.

As used herein, the term IPN refers to polymer network which comprises a network of organic or inorganic polymer chains which in some embodiments contain cross linking molecules to form a porous polymeric web within the interstitial space of a matrix. The size of the pore sizes within the web structure are theoretically defined by the length of the cross linking molecule and the distance between cross linking sites within the polymer network. When attached to a solid surface, it is preferred that at least one dimension of the polymer network theoretically exceed approximately 0.1 microns, more preferably greater than 0.5 microns and still more preferably greater than 1.0 microns. Such dimensions correspond to approximately at least 1000 atoms, more preferably at least 5800 atoms and most preferably at least 10000 atoms. The pore size of the web defined by the interstitial polymer network is chosen so as to maximize flow (by minimizing resistance) while at the same time maintaining good interaction between the IPN and solutes contained in a solution passing there through. The IPN is generally bonded to the surfaces of the solid support and is stable under the conditions of fluid flow through the composite. The IPN can be described as a solid composed of organic and/or inorganic polymer structures. The polymer network can also be a copolymer made from two or more polymerizable molecules that are copolymerized to form the IPN. The polymer network can advantageously have chemical characteristics that permit the chemical interaction of fluids or solutions flowing through the network in the interstitial spaces with the polymer network. The chemical interactions of fluids passing through the polymer network allows operations such as separation, chemical reaction, catalysis, and sorption. The polymer network is preferably composed of polymers made by polymerization methods practiced by those skilled in the art of preparing polymers.

An aspect of the present invention is the low density or concentration of the IPN, as contrasted to the density of resins and polymers in use today. Some resins, plastics, gels, and other polymeric materials known to those skilled in the art do not permit the rapid flux of fluids through the mass of the polymer substances. Fluid transport through such resins and gels is confined to flow through void regions, such as pores, in the mass of the resin substance. However, the preponderant bulk of such porous materials is actually a barrier to fluid transport, requiring that fluids pass into the resin by means of the pores or channels which have been constructed in the porous material. The interstitial polymer network of the present invention is, surprisingly, readily permeable to the flow of fluids through the mass of the IPN. The polymer networks are sufficiently thin or dilute, that they do not act as a significant barrier to fluid flow. Uniquely, the IPN's are low density solids through which fluids can readily pass.

The reasons for the preferred flow rate can be understood by consideration of the molecular weight of the functional polymerizable repeat unit in the IPN. If a polymerizable subunit had a molecular weight of 150 grams per mole, an interstitial concentration of this subunit, when converted to the polymer of the IPN, will be 30 grams per liter if the interstitial concentration (i.e., the interstitial capacity) of this molar subunit is 0.2 molar. A solution of 30 grams per liter is a 3 percent solution on a weight/weight basis in water, and will behave as a normal solution of low viscosity for most molecules. The design of the IPN is selected to make a polymer network in the interstitial spaces to be of suitably high capacity to be of practical utility, but sufficiently low to have near ideal solution behavior. The preferred interstatial molar capacity ranges of the composites are from 0.05–0.10 molar and 0.5–1.0 molar in the interstitial space (moles per liter of interstitial volume). A more preferred capacity is from 0.1–0.5 molar.

A unique aspect of the present invention is the ratio of surface area capacity of the IPN to the surface area of the solid supports. In Example 26, an ion exchange column was prepared with a capacity of 101 micromoles of polymerizable subunit of IPN per ml of column volume. The surface area, of the 11 micron beads used in that Example, is 0.38 meters per milliliter of column volume. The corresponding capacity to surface area ratio is therefore 263 micromoles of polymerizable subunit per square meter of the solid support.

By way of comparison, heterogeneous porous support materials are known in the art to have a range of surface area per mass of support material. In general, the surface area is inversely related to the size of the pores of the support. For example, typical values range from 550 square meters per gram for silica gel with 60–80 Angstrom pores to 25 square meters per gram for the 300–1250 Angstrom wide pore supports. The surface area can also be expressed in terms of area per volume of media, i.e., 8 square meters per milliliter of medium corresponds to 25 square meters per gram. Ion exchange capacities of wide pore materials (See, e.g., Girot and Boschetti, U.S. Pat. No. 5,268,097) have been reported as high as 183 micromoles per gram of support for a 300 Angstrom pore support. The ratio of capacity per square meter of surface is therefore 1.83 micromoles per square meter. The large increase in surface area capacity in the present invention amounts to a 144 fold improvement (263/1.83) over porous media manufactured by skilled artisans.

In general, it is preferred that the matrix of the invention have a surface area capacity of polymerizable subunits of IPN in excess of 5, more preferably, greater than 10, still more preferably, greater than 50, and most preferably greater than 100 μmoles of polymerizable subunit per square meter.

Advantageously, the composite matrices of the present invention make more efficient use of void volumes than do other heterogeneous support materials of known art. Known support materials are in general comprised of three phases. The solid phase, an interstitial phase, and an intraparticle phase, or pores. The interstitial phase for example, is the space between particles in chromatography beds, the first set of pores in perfusion media, and the convective transport pores of monolithic separations columns. The intraparticle phase is the volume within the pores of porous particles, the second set of pores in perfusion chromatography supports, and the plurality of side pores that comprise the majority of the surface area of monolithic columns. The volumes of the interstitial and intraparticle phases are approximately equivalent. When conventional support materials are utilized, the sorption occurs within the intraparticle phase. The interstitial phase is only used as a channel for fluid conducting fluid flow. As a result, any solute that is sorbed or concentrated inside the pores, becomes diluted upon elution into the interstitial phase in an amount proportional to the void volume of the column. The composites of the present invention have the IPN preferably in the interstitial phase. Since there almost all of the void volume is utilized in the composites of the present invention, dilution of solutes is minimized. The magnitude of this factor can be seen by comparison of advanced anion exchange materials for biochromatography with the anion exchange material disclosed in Example 26 of the present invention. The capacity of a former invention is 183 micromoles per gram of medium, corresponding to 120 micromoles per mL of void volume. The capacity of the column disclosed in Example 26 is 284 micromoles per mL of void (interstitial) volume. This 2.35 fold improvement in effective capacity will yield this benefit with increased concentration factors, and sensitivity.

A preferred set of conditions for synthesizing the composites is to conduct the in situ polymerization with low concentrations of the polymerizable molecule and that are close to the capacity goals for the composite, and to conduct the polymerization for periods of time that are sufficient to complete the conversion of monomer to polymer in high yield. The preferred concentration of polymerizable molecules for this method is from 0.1–1.0 molar. A more preferred set of conditions for synthesizing the composites is to conduct the in situ polymerization at high concentrations of the polymerizable molecules for a short time and to interrupt the polymerization before an impermeable mass of copolymer is formed in the interstitial spaces. It is believed, without relying on theory, that it is preferable to perform the polymerizations so as to produce polymer chains of high molecular weight. High concentrations of polymerizable molecules are generally favorable for the production of high mass polymers. The preferred concentrations of the polymerizable molecules used in the high concentration conditions are from 2–5 molar. More preferred concentrations are from 5 molar to neat conditions.

In another aspect of the present invention, crosslinking agents are used to increase the structural rigidity and to promote the formation of multipoint attachment of the IPN to the solid support matrix. It is known to artisans in polymer science that crosslinking of polymers can significantly affect the properties of polymeric materials. Without wishing to be bound by theory, it is probable that the IPN's of the present invention have crosslinks between functional polymer chains. The crosslinks can be formed by, for example, radical chain transfer and combination processes.

Crosslinking reagents are well known in polymer science. The crosslinking agents useful for the free radical initiated polymerizations in the present invention comprise vinyl monomers having at least one other copolymerizable group, such as double bond, a triple bond, an allylic group, an epoxide, an azetidine, or a strained carbocyclic ring. Preferred crosslinking agents having two double bonds include, but are not limited to, N,N'-methylenebis-(acrylamide), N,N-methylenebis-(methacrylamide), diallyl tartradiamide, allyl methacrylate, diallyl amine, diallyl ether, diallyl carbonate, divinyl ether, 1,4-butanedioldivinylether, polyethyleneglycol divinyl ether, and 1,3-diallyloxy-2-propanol. Since the IPN of the present invention interconnects in some embodiments solid support surfaces that may be separated by large distances on a molecular scale, preferred crosslinking agents comprise bifunctional reagents that have the crosslinking copolymerizable group attached to a polymer molecule and separated by spacers comprising from 1224 atoms long or from 120–240 atoms. More preferred crosslinking agents have polymer spacer regions from 24–120 atoms separation. The most preferred crosslinking agents are bifunctional molecules with polyethylene glycol or polypropylene glycol spacer regions that are modified at both ends with the reactive group that is capable of crosslinking with the polymer chain of the IPN. Most preferred examples of polyethylene glycol crosslinkers that are capable of free radical copolymerization are bisacrylamidopolyethylene glycol, bis-methacrylate esters of polyethelene glycol and bis 4-methylstyryl polyethylene glycol.

The preferred crosslinker concentrations range from 0.001–0.05 molar fraction of crosslinker in relation to monomer concentration. Crosslinking reagents commonly used in the art can be employed in the preparation of the composites of the present invention. A preferred length of the molecular distance between the two polymerizable groups of the crosslinker is from 20 atoms to 200 atoms. The most preferred crosslinker length is from 50–150 atoms.

A conceptual picture of the IPN is that of a common spider web. A irregular shaped spider web is a thinly crosslinked three dimensional network that is constructed between solid supports, such as solid materials. It can be appreciated that the rigidity of the spider web is a function of how long the crosslinking strands of silk are and how frequently the strands are interconnected or crosslinked. The conceptual image of a spider web is useful for creating a highly permeable, but structurally stable IPN. The molar fractions of the crosslinker used, compared to the molar concentrations of the polymerizable unit, will affect the frequency of crosslinks between the polymer chains.

The present invention is directed to a method for preparing the composites of the invention. The first step in preparing the composites is selecting a solid support which has a surface which is capable of forming strong bonds with the IPN. Many organic polymer resins possess reactivity that is favorable for grafting the IPN to the solid surface. The grafting of the IPN to the solid surface can occur by a wide variety of chemical reaction mechanisms commonly known to those skilled in chemistry. Examples of such solid support surfaces could include, without limitation, resins with amino, alcohol, thiol, hydrazine, phenyl, vinyl, carbonyl, nitrile, alkyl, silyl, oxo, nitrido, sulfido, phosphino, imino, and alkynyl functionalities. The reaction mechanisms for binding the IPN to the reactive solid surface can include free radical abstraction and addition, free radical combination, nucleophilic addition, electrophilic addition, condensation reactions, and the like. The solid support surfaces of the composites are capable of forming strong bonds with the IPN. In those aspects of the invention where the solid surface is not capable of binding with the polymer network, the solid support materials is prepared by coating the surfaces with "tether molecules", that will react with or can be elaborated into the polymer network.

Without be bound by theory, it is sometimes advantageous to modify a solid support surface with a tether molecule that confers alternative chemical functionality and/or spacially removes said chemical functionality from the surface. One method known in the art is to non-covalently coat the surface of the solid support with reagents that associate strongly with the support surface. This is particularly useful when the solid support is a metal or metalloid oxide support which has M-OH groups present at the surface. A preferred example for silica surfaces, containing an Si—OH, that will interact with bifunctional reagents bearing a positive charge at neutral pH (examples include monomers containing a cationic amine group, such as substituted amines and pyridine and the like), or molecules containing acidic hydrogen functionalities (such as alcohols, phenols, carboxylic acids, and the like). The second functional group of the bifunctional tether molecule of the present invention is capable of forming chemical bonds with the IPN by mechanisms known in the art. A preferred second functionality is an alkenyl or alkynyl group, such as vinyl, acrylic, allylic, or acetylenic moieties.

Although the tether molecules can be advantageously bound to the solid support by hydrogen bonds and the like, a preferred bond between the tether molecule and the solid support is covalent. These tether molecules are bifunctional reagents that react with one functionality with the solid support surface, and with the other functionality, form bonds with the IPN.

The most preferred tether molecule is a bifunctional reagent that is capable of forming a spacer between the support surface and the IPN. The tether molecules may be of any length, and of any chemical composition that is usefully compatible with the surface chemistry, the IPN chemistry, and the chemistry of fluids and solutions flowing through the composite matrix of the present invention. A preferred length for the tether molecule is from 15–30 atoms. More preferred tether lengths range from 30–200 atoms, although there is, in practice, no preferred upper limit. The most preferred tether molecule is amphiphilic in nature and will readily dissolve in a variety of solvents, ranging from water to hydrocarbons, and will be compatible with a variety of solution characteristics, including acidity/basicity, ionic strength, viscosity, temperature, dielectric constant, and solute and solvent reactivity. A highly preferred tether molecule is a polyether selected from, without limitation, polyethylene glycol and polypropylene glycol oligomers and polymers of various molecular weights. These are reacted with the solid surface and the IPN by methods analogous to those used with the shorter tether molecules.

Particularly stable composites of the present invention can be prepared with silica solid supports and a reactive bifunctional long tether molecule. A preferred long tether molecule is formed by reaction of polyethylene glycol with a strong base and subsequent alkylation with allyl bromide to form a monoallyl or diallyl polyethylene glycol (PEG). The said allylated polyethylene glycol is reacted with trichlorosilane to from a trichlorosilylpropyl-polethylene glycol tether molecule. This is reacted with the silanol surface to from stable siloxane bonds that comprise a highly stable solid support-tether molecule combination. The polyethylene glycol can be bound to the IPN by a variety of chemical mechanisms, such as radical abstraction from the polyethylene glycol, and initiation of IPN formation by the PEG radical. Preferred lengths for PEG are from 15–30 atoms, more preferably 30–200 atoms.

In addition to the tether molecules attached to the support surface, an optional coating of the support surface is with a "blocking reagent" to produce desirable properties on the surface, such as resistance to hydrolysis or nonspecific binding of solute molecules. For applications in which the composite is in contact with biological polymers, such as proteins or nucleic acids, a preferred blocking reagent is a trichlorosilylpropyl-oligoethylene glycol. For applications in which the surface is in contact with hydrocarbon solvents and/or solutes a preferred blocking reagent is a trichlorosilylalkane of various chain lengths. For applications where the solid support matrix may be vulnerable to attack by dissolved reagents, particularly charged acids or bases in water, a preferred blocking reagent is a carbon chain, which may or may not contain heteroatoms, and terminating with a amphiphilic functionality including, but not limited to, carboxylic acids, sulfonic acids, phosphonic acids, and amines. Most preferred is a carbon chain, which may or may not contain heteroatoms, and terminating with a siliconic acid $(RSi(OH)_3)$ functionality. The reactions involved in the preparation of the surface are performed by in situ contact of the blocking reagent with the solid support. If the solid support consists of particles, the surface preparation may be performed in a bulk mode by mixing a slurry of the support particles with the blocking reagent in an appropriate solvent.

In aspects of the present invention involving solid supports comprised of particles, the second procedure of the composite preparation is the assembly of the support into the form of the composite product matrix. A particularly simple method of assembling a solid support is to purchase fiberglass filter paper of various porosities. The particles may be assembled into a matrix by methods known to skilled artisans. Examples of the matrix assembly can include operations such as packing the particles into a column for a cylindrical matrix, dispersing the particles into a planar array that may be of any length, width, or depth, or loading them into a permeable membrane or teabag device.

The composite of the present invention is finally prepared by contacting the solid support matrix with a solution of monomers and crosslinkers and initiating reagents that will polymerize to form the IPN, or by contacting the solid support with a solution of preformed polymers and condensing or initiating reagents that crosslinked the preformed polymers to form the IPN. This is in general effected by conducting the polymerization in a manner that grafts or bonds the polymer network to the solid support with two or more points of attachment to the solid support matrix. The preferred method of constructing the IPN within the support matrix is generally conducted by in situ reactions that contact the reagents with the solid support matrix.

Suitable polymerizable subunits for the polymerization include, but are not limited to, non-ionic monomers, ionic monomers, hydrophobic monomers, hydrophilic monomers, and reactive monomers. Reactive monomers are bifunctional compounds that have a moiety capable of polymerization reactions and having a second special functional group that enables them to react with other molecules to form a wide variety of functionalized polymers. Such reactive monomers can be used by forming the polymer first, and subsequent modifications of the polymer chain. Alternatively, the reactive monomer can be utilized to form the composites of the present invention by first reacting the monomer with modifying reagent or reagents, and subsequent polymerization in situ to form to IPN.

The techniques of modifying reactive polymerizable subunits are known to those skilled in the art, are extremely versatile, and can be used to prepare composites for use in affinity chromatography, catalysis, ligand exchange chromatography, chemical synthesis, nucleic acid and peptide synthesis, aqueous metal and non-metal ion extraction, and other heterogeneous operations to skilled artisans.

In some embodiments the polymerizable subunit is incorporated into the IPN which contains a functional group. As used herein, a "functional group" refers to a moiety which is capable of interacting with a member of a binding pair or a reactive moiety so as to include such molecules into the IPN. Generally, the linkage between such molecules in the functional group can be covalent or electrostatic in nature. For example, an ionic exchange matrices can be used to bind a positively charged chemical catalyst to provide a catalytic matrix. Alternatively, for example, a member of a binding pair, e.g., streptavidin or biotin can be immobilized covalently to a functional group in the IPN to provide for an affinity matrix.

An exceptionally diverse class of functional groups comprise ligands that have available electrons for covalent interaction with or binding to various metals. Composites prepared with functional groups that are metal-binding ligands can be used for a wide variety of chemical reagents known to skilled artisans, such as immobilized chemical reagents, catalysts, metal sorption media, metalloprotein binding, and the like.

As used herein, a binding pair refers to not only binding pairs but multimeric complexes. For example, a member of a binding pair can include acid and basic molecules which can be electrostatically reactive with their counterparts at appropriate pH. Binding pairs also include receptors-ligand complexes, multimeric protein complexes, protein-nucleic acid complexes and the like.

As used herein, a "reactive moiety" refers to a moiety which is chemically, enzymatically or catalytically reactive. Examples of moieties which can be immobilized in the IPN include enzymes such as proteases, kinases and nucleic acid restriction enzymes, chemical catalysts such as metal-ligand complexes, phosphine-palladium complexes, and redox catalysts, and chemical reagents for nucleic acid, protein and combinatorial chemistry synthesis. In addition, the reactive moiety can be a chemically reactive group which can act as starting material for solid phase organic synthesis.

In another aspect of this invention, anionic IPN's will create anionic sorbent composites (i.e., cationic exchange materials). The functional groups that are the substituents on the vinyl monomer can be carboxylate groups from acrylic acid or methacrylic acid, sulfonate groups from acrylamidomethyl-propane sulfonic acid or vinyl sulfonic acid, or phosphate groups from N-phosphoethyl-acrylamide. Alternatively, anionic composites can be prepared from a neutral monomer containing nucleophilic functionalities, such as polyvinyl acetate that is partially of fully hydrolyzed after polymerization to create a polyvinyl alcohol IPN which can be activated with an aryl or alkanesulfonyl halide reagent. After polymerization to form the electrophilically activated IPN, the composite is modified by reaction with an appropriate electrophilic reagent, including, but not limited to, bromoacetic acid, succinic anhydride, or bromoethane-sulfonic acid. Likewise, anionic composites can be prepared from neutral monomers containing electrophilic functionalities, including, but not limited to, vinyl bromide, vinyl chloride, vinyl acetate which is polymerized and then hydrolyzed to polyvinylalcohol, allyl bromide, 4-chloromethylstyrene, glycidylmethacrylate, or 4-bromostyrene. The monomers are first polymerized in the solid support matrix to create an activated IPN, which is subsequently modified by reaction with an appropriate nucleophilic reagent, including, but not limited to, mercaptoacetic acid, hydroxyacetic acid, or iminodiacetic acid. The methods of the present invention can also make use of cationic monomers to create anion exchange composites, including the following functional monomers having substituted amino groups (e.g. diethylaminoethyl methacrylamide, diethylaminoethyl acrylamide, methacrylamidopropyltrimethylammonium halide, triethylaminoethyl acrylamide, trimethylaminoethyl methacrylate, dimethylaminoethyl methacrylate), or heterocyclic amines (e.g. 2-vinylpyridine, vinylimidazole, 4-vinylpyridine, diallyldimethylammonium halide). Non-ionic polymers in the IPN may be synthesized from: acrylamide, hydroxy-containing acrylamide derivatives (e.g. N-tris-hydroxymethyl-methyl acrylamide, methaloyl acrylamide, dimethyl acrylamide, 2-hydroxethylacrylamide, N-acryloylmorpholine), methacrylamide, hydroxy-containing methacrylamide derivatives, heterocyclic neutral monomers (e.g. vinylpyrrolidone, N-acryloylmorpholine), or hydroxy-containing acrylates.

The methods of the present invention can also be used to make use of cationic monomers to create anion exchange composites, by similar synthetic methods as described for the preparation of the anionic matrices. These monomers can be monomers, which upon polymerization, will form a cationic polymer matrix. These monomers include, but are not limited to, N-methylvinylpyridinium, diallyldimethylammonium halide, acrylamidopropyltrimethylammonium, and allylamine. Alternatively, cation IPN's can be synthesized by polymerization of an electrophilic monomer, followed by reaction with a nucleophilic compound that either results in or can be elaborated into a cationic composite. These monomers may include, but are not limited to, the following functional groups: polyvinyl bromide, polyvinyl chloride, polyvinylalcohol-methanesulfonate ester, polyallyl bromide, polychloromethylstyrene, polyglycidylmethacrylate, or poly-4-bromostyrene. Suitable nucleophiles for subsequent derivitization include, but are not limited to, cyclic or acyclic amines (e.g. ethylene diamine, triethylamine, trimethylamine, ammonia, mercaptoethylamine, diethylmercaptoethylamine, pyridine, morpholine, polyethylene imine or oligomers thereof, hydroxyethylamine, bis(hydroxyethylamine), aniline, vinylamine, or iminodiacetic acid), phosphines (e.g. triphenylphosphine, trimethylphosphine, bis(diphenylphosphino)ethane, and other alkyl or aryl phosphines, or dialkyl sulfides (e.g. dimethyl sulfide, or diphenyl sulfide).

According to the aspects of the present invention involving radical polymerizations to form the IPN, polymerization is effected in the presence of an effective amount of a polymerization initiator, for example, thermal initiators such as ammonium persulfate/tertiary amine, nitrites or transition metals. Other examples include 2,2'-azobis(2-amidinopropane) hydrochloride, potassium persulfate/dimethylaminopropionitrile nitrile, 2,2'-azobis-(isobutyronitrile), 4,4-azobis(4-cyanovaleric acid), or benzoylperoxide. Polymerization begins, as is known in the art, e.g., with agitation, exposure to heat, or exposure to a sufficient amount of radiant energy.

The polymerization is also conducted in a manner that forms a polymer network that is permeable to the flow of fluids and solutions through it. Although the chemistry of the polymerization reactions are well know to polymer chemists of normal skill, it is surprising that the polymerization reactions disclosed herein produce a resin, herein defined as the interstitial polymer network, of very low density of polymer materials as defined by mass of polymer network per unit volume of the void volume of the composite, and which is not a barrier to fluid flow, as are other solids. It can be appreciated that an IPN will be more permeable to solvent flow if the functional polymers and crosslinkers that comprise the IPN are high molecular weight and have a low frequency of crosslinks. Methods that are known to practitioners of polymer preparation for increasing polymer molecular weight include low initiator concentrations, relatively low initiation temperatures for thermally initiated radical polymerizations, high monomer concentrations, reduced concentrations of radical scavengers or inhibitors in the polymerization mixture, use of solvents with low chain transfer reactivity, and the like. One method for synthesizing the low density polymer network is to conduct the polymerization with low concentrations of the polymerizable components in the reaction. Preferred concentrations of the polymerizable components of the in situ IPN-forming reaction are from 0.05–0.10 molar. More preferred concentrations of polymerizable molecules are 1.0–2.0 molar. Most preferred monomer concentrations are from 0.1–1.0 molar. It can be appreciated that the most favorable concentrations of polymerizable molecules for preparing the IPN will, to some extent, depend upon the chemical constitution of the molecule. The preferred amount of free radical initiator is from 0.1–1.0 molar percent of the concentration of the polymerizable molecule.

Another method to create high molecular weight polymer chains in the IPN is to conduct the polymerization at concentrations from 2.0 molar to neat and to interrupt the polymerization process at low monomer to polymer conversion levels.

The next step of preparation of the composites of the present invention is accomplished by flushing the composite with appropriate solvents or solutions that remove any polymerizable molecules, polymers, or copolymers that are not strongly bound to the composite.

It can be readily appreciated that there are numerous parameters involved in the composites of the present invention. The overall objective of synthesizing the composites of the present invention is to enable chemical operations, that heretofore have been done in either solution or in heterogeneous modes, be performed with the advantages of both the kinetics of homogeneous reactions and the operational convenience of a heterogeneous solid phase system. The objective of combining the advantages of heterogeneous and homogeneous systems is accomplished with the interstitial polymer network, that permits fluids, solutions, and solutes to flow freely through the polymer network and experience chemical interactions with functional groups on the polymer network, unhindered and unaffected by any interactions with a solid surface. It is also preferable for the IPN to have a high capacity of functional groups. However, without wishing to be limited by theory, it is probable that steric crowding of functional groups will reduce their reactivity and alter the nature of the performance of the composites. It is therefore possible that high capacity of the functional groups on the IPN can be disadvantageous in some applications of the invention. Low capacities reduce the economic and operational utility of the composites, whereas overly high capacities can reduce permeability and fluid flow through the composite.

Uses of the composites of the invention will employ flow rates of fluids through the IPN's that can advantageously be very fast. The convective fluid flow through IPN will allows the use of flow rates that are not available with existing art. The flow rate of the affinity chromatographic process shown in FIG. 4 was 7300 cm per hour. Preferred flow rates for chromatographic separations employing the composites of this invention are from 100–2000 cm per hour. More preferred flow rates will range from 2000–10,000 cm per hour. It can be appreciated that use of the composites for other processes, such as chemical catalysis or synthetic chemistry and the like, will be limited by the kinetics of the chemical reactions occurring. Preferable flow rates will be adjusted so that the residence time of a reacting species in the composite matrix will be from 4–10 half lives of the analogous reaction conducted in solution phase.

The above described matrix can be deployed in a variety of chemistry formats, depending upon the nature of the chemical modifications of the IPN. In this regard the composites can be used for solid supported chemical synthesis operations. Synthesis procedures can be employed for synthesis of oligonucleotides, peptides, combinatorial chemistry libraries, and other substances that are adaptable to solid supported synthesis arrays. Such solid supported synthesis composites can be used in a series or more preferably in a parallel fashion. Preferred embodiments of parallel synthesis composites include microtiter plates equipped with a porous glass fiber frit in the bottom of the wells of the microtiter plates. Preferred porosities for the frits are from 1–20 microns. The interstitial volumes in the pores of the frits can be modified with an IPN that is chemically modified so as to provide an appropriate reactive group for initiating solid phase chemical synthesis procedures. A more preferred embodiment of the microtiter plate format of the composites of the present invention will make use of small quantities, varying from 10–100 milligrams, of nonporous beads, that are preferably 5–40 microns in diameter, in a microtiter plate, thus making a parallel series of minicolumns after the IPN matrix has been synthesized by the methods of the invention. A most preferred embodiment of the parallel synthesis composites is a matrix of glass fibers (filter paper) with preferred pore diameters of 5–40 microns, that has been bound with an IPN that is suitably substituted with moieties useful for initiating solid phase synthesis procedures. A planar array made with porous filter paper and substituted with a IPN in the solid matrix can be used for massively parallel operations that are limited only by the spot size of the array synthesis instrument device.

Preferred embodiments of parallel composites for nucleic acid synthesis, are polymer networks with primary alcohol, amino, or carboxylate functional groups that can serve as the starting points for nucleic acid synthesis, as is commonly practiced in synthesis instruments. Other highly preferred embodiments of solid phase synthesis uses include the preparation of arrays of oligoncleotides, peptides, or combinatorial libraries. Techniques for creating microarrays by spotting technologies or even ink jet deposition of reagents are known in the art and are readily adaptable to the IPN composites of the present invention.

It can be appreciated that IPN's of a great variety of structures can be prepared by the methods disclosed in the present invention, but using other polymer chemistries and methods of forming polymers.

As practiced herein, the polymer network has practical and commercial utility for its ability to perform the various operations known to those knowledgeable of chromatography, separations, catalysis, solid supported chemical synthesis, sorption and other heterogeneous chemical procedures. In general, the present invention makes use of known chemical processes and chemical functional groups on the polymer network. In such cases, the composites of the present invention are modified or repeatedly modified by chemical reactions carried out with the polymer network.

EXAMPLES

Example 1

Preparation of Trichlorosilyl Activated Polyethylene Glycol

Figure 2:
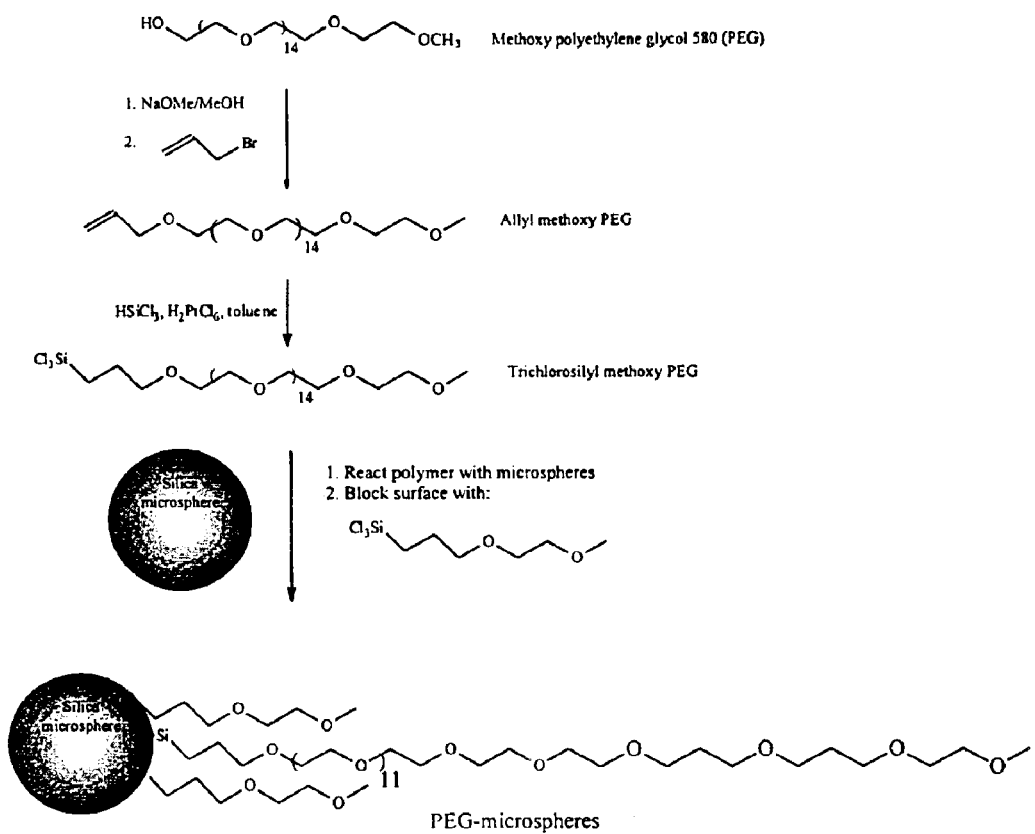
FIG. 2 shows the reactions used for preparing trichlorosilyl activated polyethylene glycol described in Example 1, of silanization of silica microspheres with the PEG tether molecule in synthesized in Example 2, and blocking of the surface with the trichlorosilylpropyl ethylene glycol methyl ether blocking reagent.

Methoxypolyethylene glycol 580 (37.5 grams, 65 mmoles) was dissolved in 125 ml methanol and deprotonated with sodium methoxide (4.22 grams, 78 mmoles). When the sodium methoxide had dissolved, 7.0 ml of allyl bromide (9.8 grams, 81 mmoles) was dripped into the reaction mixture with a dropping funnel. The mixture was stirred overnight and was filtered into a 500 ml round bottom flask. The solvent was removed by a rotary evaporator and redissolved in 150 ml of toluene. The suspension was filtered and evaporated to give 40 grams of an oil, the allylmethoxy polyethylene glycol. Toluene (88 ml) was added to the residue and a 6.2 ml of a 0.01 molar solution of chloroplatinic acid in tetrahydrofuran was added. Trichlorosilane (6.2 ml) was added and the reaction was stirred overnight under a nitrogen atmosphere. It was heated to 55 degrees for two hours and then cooled and stored under nitrogen in the refrigerator. The reactions are shown in FIG. 2.

Example 2

Preparation of Trichlorosilylpropyl Ethylene Glycol Methyl Ether

Ethylene glycol monomethyl ether (352 grams) was dissolved in 210 ml ether and deprotonated with 235 grams sodium methoxide. When the sodium methoxide had reacted, 400 ml of allyl bromide was dripped into the reaction mixture with a dropping funnel. The mixture was stirred overnight and poured into water. Saturated sodium chloride was added and the water was extracted 3 times with ether (200 ml). The ether was dried over magnesium sulfate and was filtered into a 1000 ml round bottom flask. The solvent was distilled off by a rotary evaporator and the allyl ether was redissolved in 200 ml of toluene. An 8 ml solution of chloroplatinic acid (8 mg/ml in tetrahydrofuran) was added. Trichlorosilane (72 ml) was slowly added by dropping funnel and the reaction was stirred overnight under a nitrogen atmosphere. The solution was heated to 55 degrees for two hours and then cooled and stored under nitrogen in the refrigerator.

Example 3

Preparation of 10 Micron Polyethylene Glycol-Modified Silica

Hollow glass spheres (Aldrich, 11 micron, 105.4 g) were placed in a 500 ml round bottom flask and dried in an oven controlled at 150° C. for 12 hours. The flask was removed from the oven, stoppered, and cooled to room temperature under nitrogen. Toluene (160 ml) and 20 ml of the reagent prepared in Example 1 were added. Triethylamine (2.5 ml) was added and the flask was then agitated by rotation for 12 hours at room temperature. The reagent solution from Example 2 (10 ml) was added and the flask was rotated for another 4 hours at room temperature. The reaction mixture was filtered on a coarse fritted glass funnel and washed three times each with 100 ml portions of methanol, ether, methanol, and ether. FIG. 2 shows the reactions and indicates the coating of the nonporous spheres.

Example 4

Preparation of Bis-acrylamido PEG 1900 Crosslinker

O,O'-Bis(2-aminoethyl)polyethylene glycol 1,900 (30 grams, 9.84 mmoles) was dissolved in 61 mL of dichloromethane in a round bottom flask equipped with a magnetic stir bar. Triethylamine (2.75 mL, 19.7 mmoles) was added, and the flask was purged with dry nitrogen. Acryloyl chloride (1.75 mL, 21.5 mmoles) was added to the stirred solution over 10 minutes reaction time. The reaction mixture was filtered into a round bottom flask and the volume was reduced to approximately 50 mL on a rotary evaporator. Ethyl ether was added with swirling until the solution became cloudy, and the mixture was cooled to −20 deg overnight. The first crop of crystals of the bis-acrylamido PEG was harvested by filtration. The remaining yield of product was purified by repeated crystallization from dichloromethane-ether.

Example 5

Preparation of a Composite Matrix by Polymerization of 0.5 Molar Hydroxyethyl Methacrylate (HEMA)

The 11 micron polyethylene glycol-modified silica prepared in Example 3 was pressure packed with water into four 4.6×33 mm HPLC columns by standard methods used for packing high performance columns. The column ends were fitted with end fittings and frits. A 0.003 molar solution of the radical initiator, 2,2'-azobis (2-methylpropioniamidine) dihydrochloride (15.9 mg), in 20 ml of degassed water was prepared. Bis-acrylamido PEG 1900 (0.11 g, 0.055 millimoles), prepared by the method of Example 4 was dissolved in 18 ml of the initiator solution and hydroxyethyl methacrylate (0.474 g, 3.65 mmoles) was added. The polymerization solution was injected into the columns with a syringe equipped with a HPLC column adaptor (Upchurch Scientific) and then the ends of the columns were plugged. The columns were immersed in a 61 degree water bath for 21 hours to perform the graft polymerization reaction. The reaction was terminated by removing the column from the bath and flushing it with water, using an HPLC pump. The backpressure in the column at a flow rate of 1.0 mL/minute was approximately 900 psi. This is much higher than the backpressure normally observed for columns with this particle size and column length, which is normally 130 psi, and indicated that the concentration of monomer used is too high and the permeability of the IPN is quite low. The methacrylate ester was partially hydrolyzed to polymethacrylic acid by injecting 1.0 molar nitric acid into the column for 24 hours. Titration of the carboxylic acid groups by cupric ions at a flow rate of 2.4 mL/minute (1773 cm/hour) determined the capacity of the column was 0.19 moles/liter of interstitial volume.

Example 6

Preparation of a Composite Matrix by Polymerization of 0.3 Molar Hydroxyethyl Methacrylate (HEMA)

The 11 micron polyethylene glycol-modified silica prepared in Example 3 was pressure packed with water into two 4.6×33 mm HPLC columns by standard methods used for packing high performance columns. The column ends were fitted with end fittings and frits. The radical initiator, 2,2'-azobis (2-methylpropioniamidine) dihydrochloride (18.3 mg) was dissolved in 23.5 ml of degassed water. Bis-acrylamido PEG 1900 (0.102 g, 0.051 millimoles), prepared by the method of Example 4 was dissolved in the initiator solution and hydroxyethyl methacrylate (0.6518 g, 5.01 mmoles) was added. The monomer and crosslinker solution was injected into the columns with a syringe equipped with a HPLC column adaptor (Upchurch Scientific) and then the ends of the columns were plugged. The columns were immersed in a 61 degree Centigrade water bath for 24 hours to perform the graft polymerization reaction. The reaction was terminated by removing the column from the bath and flushing it with water, using an HPLC pump.

Example 7

Measurement of Nonspecific Protein Binding of the HEMA Interstitial Polymer Network Composite of Example 5

Figure 3:
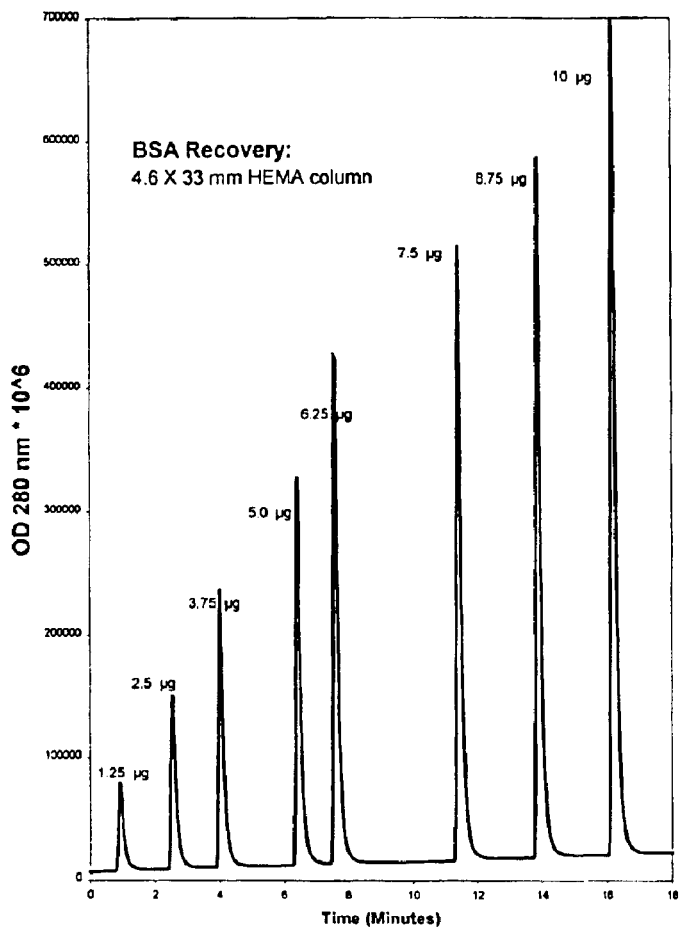
FIG. 3 is a chromatogram showing the results of the test for nonspecific binding of bovine serum albumin (BSA) in an IPN made by copolymerizing HEMA. Each peak corresponds to void volume peaks from injections respectively of 1.25, 2.5, 3.75, 5.0, 6.25, 7.5, 8.75, and 10.0 micrograms were injected. The flow rate was 0.6 mL per minute. A graph of the integrated peak areas as a function of micrograms BSA injected is in the lower panel of FIG. 3.
Figure 3:
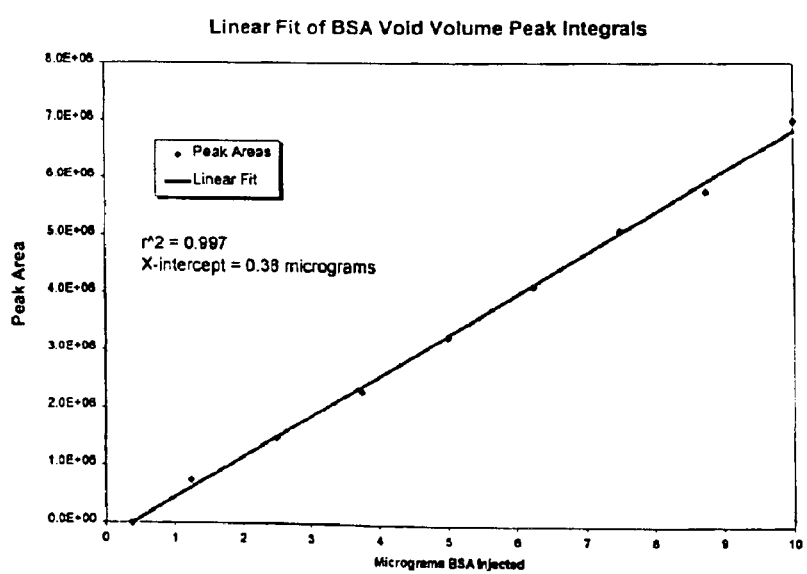

The column prepared in Example 7 was plumbed into an HPLC and equilibrated with 0.01 M sodium phosphate, 0.15 M NaCl buffer at pH 7.5. A series of eight injections of 20 ul of bovine serum albumin were injected at concentrations such that (1.25, 2.5, 3.75, 5.0, 6.25, 7.5, 8.75, and 10.0) micrograms were injected. The chromatogram showing the eight injections is shown in FIG. 3. A graph of the integrated peak areas as a function of micrograms BSA injected is in the lower panel of FIG. 3.

Example 8

Oxidation of Interstitial HEMA Polymer to Aldehyde Functionality

A solution of 0.5 M acetic anhydride in DMSO was injected into two columns prepared in Example 5 and allowed to react overnight. The reactions were terminated by flushing with water.

Example 9

Preparation of Interstitial Protein A Column

The column of Example 7 was injected with a solution of 5 mg/ml Protein A (Repligen) and 20 mg/ml sodium cyanoborohydride in water. After 2 hours of reaction, the column was flushed out and tested for performance.

Example 10

Figure 4:
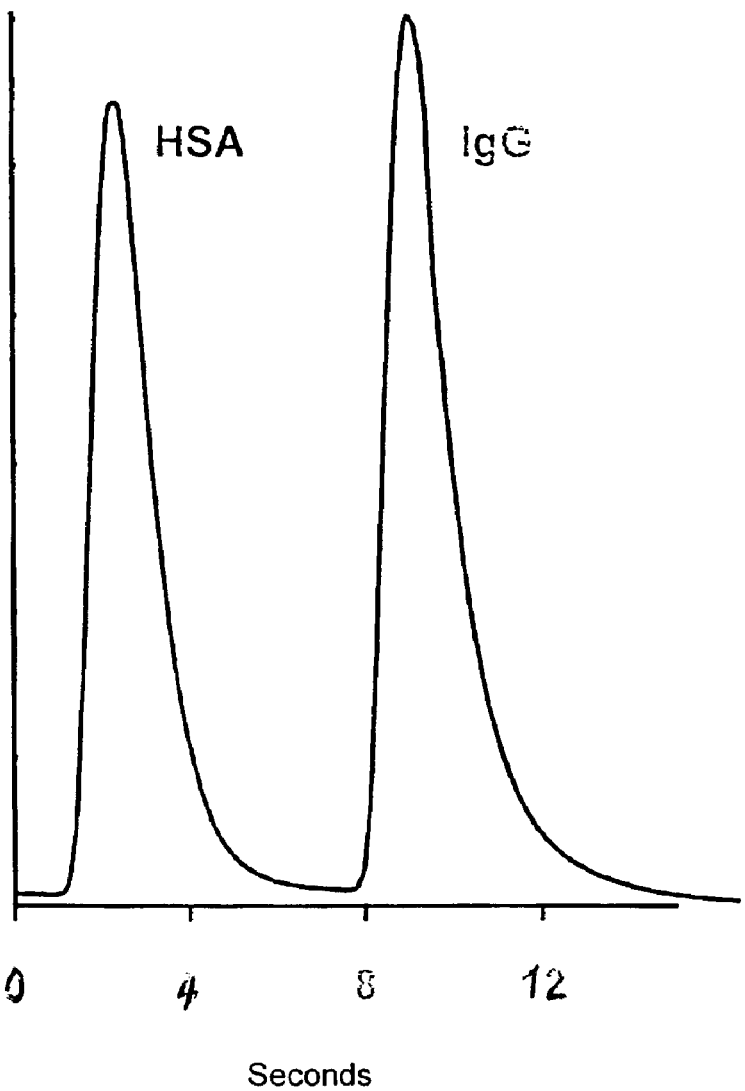
FIG. 4 shows an affinity chromatographic separation of albumin and human immunoglobulin. The Protein A column was equilibrated with neutral phosphate buffered saline at a flow rate of 7300 cm/hour. A solution of albumin and IgG (1.0 mg/ml of each protein, 50 μL) was injected into the column. The IgG bound to the column, and the albumin was rinsed out in ~4 seconds. At 4 seconds, the elution buffer was pumped into the column (at 7300 cm/hour) and the IgG eluted with a peak maximum at ~10 seconds.

Separation of IgG from Human Serum Albumin at High Flow Rates in the IPN Protein A Column The Protein A column was equilibrated with neutral phosphate buffered saline at a flow rate of 7300 cm/hour. A solution of albumin and IgG (1.0 mg/ml of each protein, 50 $\mu$L) was injected into the column. The chromatogram is shown in FIG. 4. The IgG bound to the column (shown by other experiments, such as FIG. 3), and the albumin was rinsed out in 4 seconds. At 4 seconds, the 20% acetic acid elution buffer was pumped into the column (at 7300 cm/hour) and the IgG eluted with a peak maximum at ~10 seconds.

Example 11

Preparation of a Composite with 0.22 Molar Methyl Acrylate Interstitial Polymer Networks The 11 micron polyethylene glycol-modified silica prepared in Example 3 was pressure packed with water into a 4.6×33 mm HPLC column by standard methods used for packing high performance columns. The columns ends were fitted with end fittings and frits. The column was flushed with methanol and then ethyl acetate. A 0.0053 molar solution of the radical initiator, AIBN (19.6 mg, 0.12 mmoles) and bis-acrylamido PEG 1900 (0.10 g, 0.0050 millimoles), in 22.5 ml of degassed ethyl acetate was prepared. Methyl acrylate (0.218 g, 2.53 mmoles) was added to a 9.5 ml portion of the solution. This copolymerization solution was injected into the columns and the ends of the columns were plugged. The columns were immersed in a 61 degree water bath for 16 hours to perform the graft polymerization reaction. The reaction was terminated by removing the column from the bath and flushing it with acetone.

Example 12

Conversion of the Poly Methyl Acrylate IPN of Example 11 to a Metal Chelating Functionality and Measurement of the Composite's Capacity by Titration with Copper(II) Ions A tetrahydrofuran solution of 0.75 molar diethylenetriamine and 0.0375 molar dimethylaminopyridine pyridine was prepared and injected with a syringe into one of the columns made in Example 11. The column end was plugged and the ester to amide conversion was allowed to proceed for six hours. A second injection of the solution was made into the column and the column was allowed to react overnight, for a total reaction time of 20 hours. The column was rinsed out with water and the capacity of the column for chelating copper was measured to determine the quantity of amide formed. The capacity of the column was measured by plumbing the column into an HPLC equipped with four pumps and a UV-visible detector. The flow rate used was generally 1.2 mL/minute per mL of total column volume. The columns were equilibrated by one cycle of: 1.0 M nitric acid, water, 0.1 M ammonia, and water. Copper sulfate (0.01 molar) was pumped into the column and the effluent of the column was monitored by a UV-visible detector set at 799 or 800 nm. The capacity of the column, as shown by the adsorption isotherm, was 0.067 moles/liter of interstitial volume. The combined yield of the reaction sequence of polymerization and ester to amide conversion was therefore 30.4% (0.067/0.22).

Example 13

Modification of Glass Fiber Filter Disk with a Polyethylene Glycol Tether Molecule Glass fiber membrane cartridges (Gelman membrane filter disk, purchased from Aldrich) were treated with 2.0 ml of the trichlorosilyl polyethylene glycol reagent solution prepared in Example 1 by injecting the solution into the cartridges and sealing the Leur fittings at the inlet and outlet with plugs. After 8 hours of reaction, the membranes were washed with toluene and then methanol.

Example 14

Preparation of a Composite Membrane Matrix with Polyacrylic Acid Interstitial Polymer Networks The radical initiator, 2,2'-azobis (2-methylpropioniamidine) dihydrochloride (11.9 mg) and bis-acrylamido PEG 1900 (0.248 g, 0.12 millimoles, prepared by the method of Example 4) were dissolved in 9.9 ml of degassed water. Acrylic acid (0.405 g, 5.62 mmoles) was added to make up a 0.56 molar solution of the monomer. The monomer and crosslinker solution was injected into the filter discs, prepared in EXAMPLE 13, with a syringe and then the inlet and outlet of the cartridge were plugged. The cartridge was immersed in a 68 degree Centigrade water bath for 21 hours to perform the graft polymerization reaction. The reaction was terminated by removing the unit from the bath and flushing it with water. Unreacted and ungrafted materials were flushed from the cartridge by three cycles of rinsing with 1.0 M nitric acid, water, 0.1 M ammonia, and water. The capacity of the membrane unit was determined to be 4.8 micromoles. Using the 0.04 mL void volume of the pores in the membrane specified by the manufacturer, the capacity of the membrane is 0.12 moles of carboxylic acid per liter.

Example 15

Preparation of a Composite Membrane Matrix by Polymerizing Neat Glycidyl Methacrylate to Make a Planar Interstitial Polymer Network A solution of 0.006 molar radical initiator, AIBN, was prepared in 30 mL glycidyl methacrylate. Bis-acrylamido PEG 1900, prepared by the method of Example 4, was added until the solution was saturated in the crosslinker (approximately a 25% w/w solution). Approximately 200 mg of basic alumina was added to adsorb the inhibitor, and the suspension was agitated and degassed for 45 minutes by bubbling nitrogen into it. The suspension was allowed to settle for 5 minutes, and the supernatant initiator, monomer and crosslinker solution was withdrawn with a syringe and injected into a filter disc prepared in EXAMPLE 13. The inlet and outlet of the cartridge were plugged. The cartridge was immersed in a 71 degree Centigrade water bath for 20 minutes to perform the graft polymerization reaction. The reaction was terminated by removing the unit from the bath and flushing it with acetone.

Example 16

Preparation of a Amino-Substituted Composite Membrane Matrix by Reacting the Poly Glycidyl Methacrylate IPN with Ethylenediamine A 1.0 molar ethylenediamine solution in methanol was prepared and injected with a syringe into the cartridge prepared in EXAMPLE 15. The cartridge end fittings were plugged and the reaction of the amine with the polyepoxide was allowed to proceed for two hours at room temperature. The reaction was terminated by flushing the column with methanol, acetonitrile, and dichloromethane.

Example 17

Preparation of an Oligonucleotide Synthesis Composite Derivatized with 5'-Dimethoxytrityl-Thymidine A solution of dicyclohexyl carbodiimide (0.538 grams), dimethylaminopyridine (0.0956 grams) and 5'-O-(4,4'-dimethoxytrityl)thymidine 3'-O-succinic acid (0.2264 grams) was prepared in 3.0 ml of dry dichloromethane. A portion of the solution (200 microliters) was injected into an amino-substituted filter disk prepared in EXAMPLE 16. The cartridge end fittings were plugged and the reaction was allowed to proceed for 20 hours at room temperature. The cartridge was rinsed out with 40 ml of dichloromethane. To ensure that the column was completely rinsed free of any noncovalently bound dimethoxytrityl thymidine, the last 5 mL effluent from the rinse was treated with an equal volume of 2% trichloroacetic acid in dichloromethane. No orange color from the trityl cation was detectable. To quantify the 5'-O-(4,4'-dimethoxytrityl)thymidine 3'-O-succinic acid that was immobilized in the column, the column was rinsed with 2% dichloroacetic acid in dichloromethane. The effluent solution volume was determined and the optical absorption at 498 nm was measured. By this method, the quantity of trityl groups immobilized to the IPN in the membrane cartridge was determined to be 199 micromoles.

Example 18

Preparation of 40 Micron Polyethylene Glycol-modified Silica Microspheres

Hollow glass spheres (3M Corp, S32 microspheres, 137.3 g) were placed in a 500 ml round bottom flask and dried in an oven controlled at 150° C. for 12 hours. The flask was removed from the oven, stoppered, and cooled to room temperature under nitrogen. Toluene (75 ml) and 17 ml of the trichlorosilane-PEG reagent prepared in Example 1 were added. Triethylamine (9.0 ml) was added and the flask was then agitated by rotation for 12 hours at room temperature. The reagent solution from Example 2 (10 ml) was added and the flask was rotated for another 4 hours at room temperature. The reaction mixture was filtered on a coarse fritted glass funnel and washed three times each with 100 ml portions of methanol, ether, methanol, and ether.

Example 19

Preparation of Composite Columns with 35 Micron Microspheres andNeat Glycidyl Methacrylate Disposable BioFlash chromatography columns from Biotage Corp. (Charlottesville, Va.) to prepare the composites in. The columns have 1.0 mL bed volume and are 1.0 cm long. The PEG-coated microspheres prepared in EXAMPLE 18 were packed in the columns and polypropylene frits were installed at both ends of the bed. The supernatant initiator, monomer and crosslinker solution prepared in EXAMPLE 15 was injected into the columns. The columns were immersed in a 71 degree Centigrade water bath for 20 minutes to perform the graft polymerization reaction. The reaction was terminated by removing the unit from the bath and flushing it with acetone.

Example 20

Preparation of an Amino-Substituted Composite Chromatography Column by Reacting the Poly Glycidyl Methacrylat IPN with Ethylenediamine A 1.0 molar ethylenediamine solution in methanol was prepared and injected with a syringe into the column prepared in EXAMPLE 19. The cartridge end fittings were plugged and the reaction of the amine with the polyepoxide was allowed to proceed for two hours at room temperature. The reaction was terminated by flushing the column with methanol, acetonitrile, and dichloromethane. The capacity of the column was measured by copper (II) ion titration and determined to be 0.12 moles of amine nitrogens per liter of interstitial volume.

Example 21

Addition of Trichlorosilane to Polybutadiene

Polybutadiene, (5.0 grams) molecular weight 420,000 (Aldrich Chemicals) was dissolved in dry toluene (114.2 grams). Chloroplatinic acid catalyst solution (50 microliters of a 10 mg/mL solution in THF was added. The solution was vigorously stirred under dry nitrogen while 12 microliters of trichlorosilane were added. The solution was allowed to react 2 hours and room temperature. It was then stored under dry nitrogen at −20 degrees.

Example 22

Silanization of Sand with Trichlorosilyl Polybutadiene

Quartz beach sand (91.5 grams, Aldrich Chemicals, 20 micron average irregular particle size) was dried in an oven at 150 deg for 24 hours in a round bottom flask. The sand was cooled to room temperature under dry nitrogen and suspended in 86 ml dry toluene. A solution of trichlorosilyl polybutadiene in toluene (40 mL), prepared by the method of EXAMPLE 21, was added. Pyridine (30 ml) was added and the flask was rotated under nitrogen for 24 hours. The polybutadiene coated sand was worked up by filtering and washing with toluene, and drying.

Example 23

Figure 5:
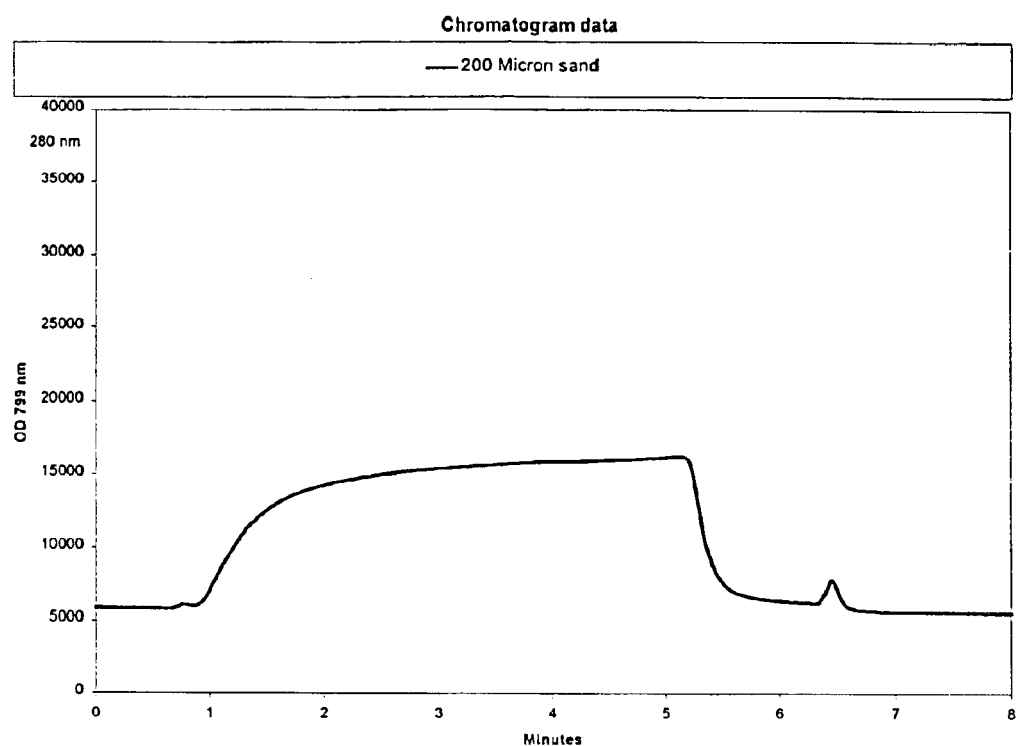
FIG. 5 The top panel of FIG. 5 is the copper adsorption and elution chromatogram measured with the column that had no bis-acrylamido PEG crosslinker, prepared in Example 23, and shows a very small copper elution peak at 6.5 minutes. The capacity of this column was very low and less than 0.01 moles of carboxylate per mL of interstitial void volume. The lower panel of FIG. 5 shows the chromatogram for the column with the bis-acrylamido PEG crosslinker. The large copper elution peak at 14.5 minutes shows the high capacity of this IPN.
Figure 5:
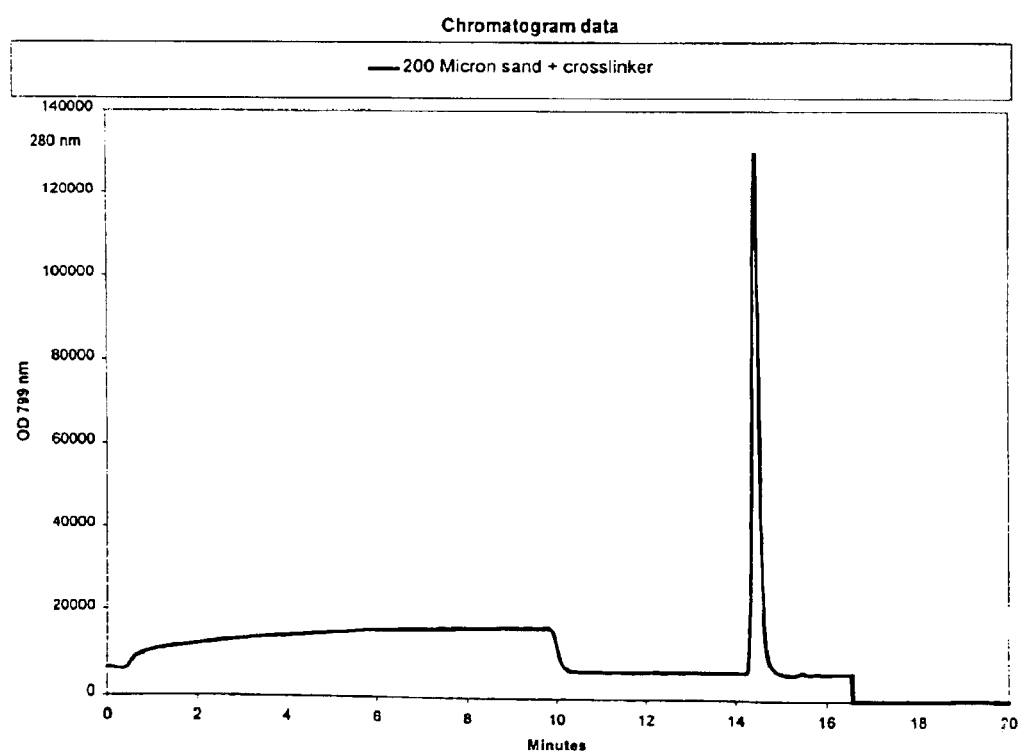
Figure 6:
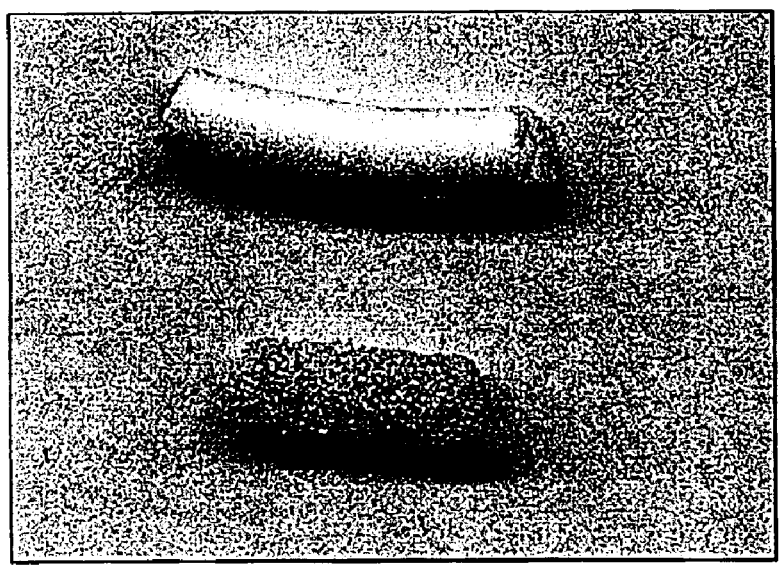
FIG. 6. The pellet in the bottom of FIG. 6 shows is a portion of the extruded crosslinked composite prepared in Example 23. The cylinder in the top of FIG. 6 is a scan of an interstitial composite that was extruded from a column made with 11 micron microspheres, acrylic acid, and the bis-acrylamido PEG crosslinker.
Figure 7:
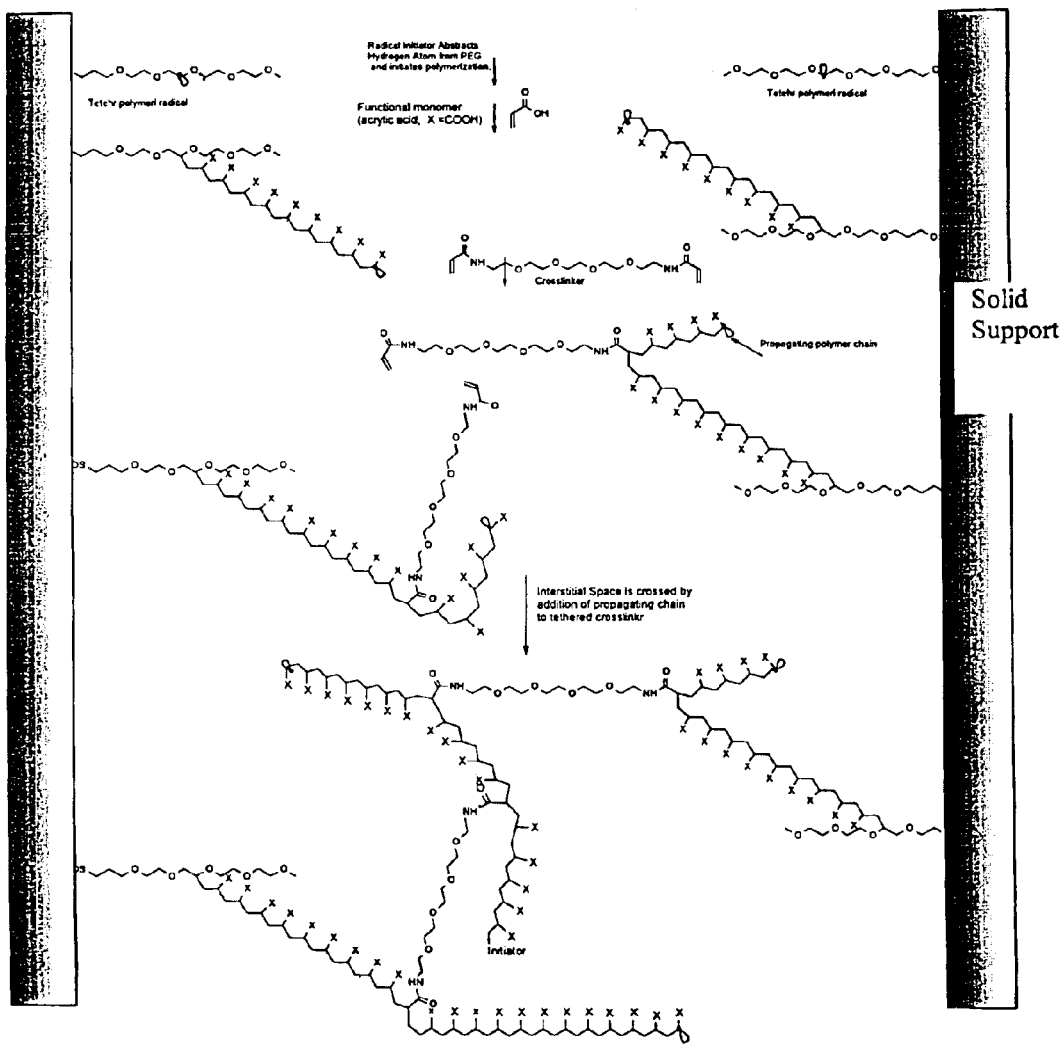
FIG. 7. Shows a presumptive mechanism by which polymer grafting occurs with a polyethylene glycol tether polymer and crosslinking of the IPN forms at least a two point connection with the solid support.
Figure 8:
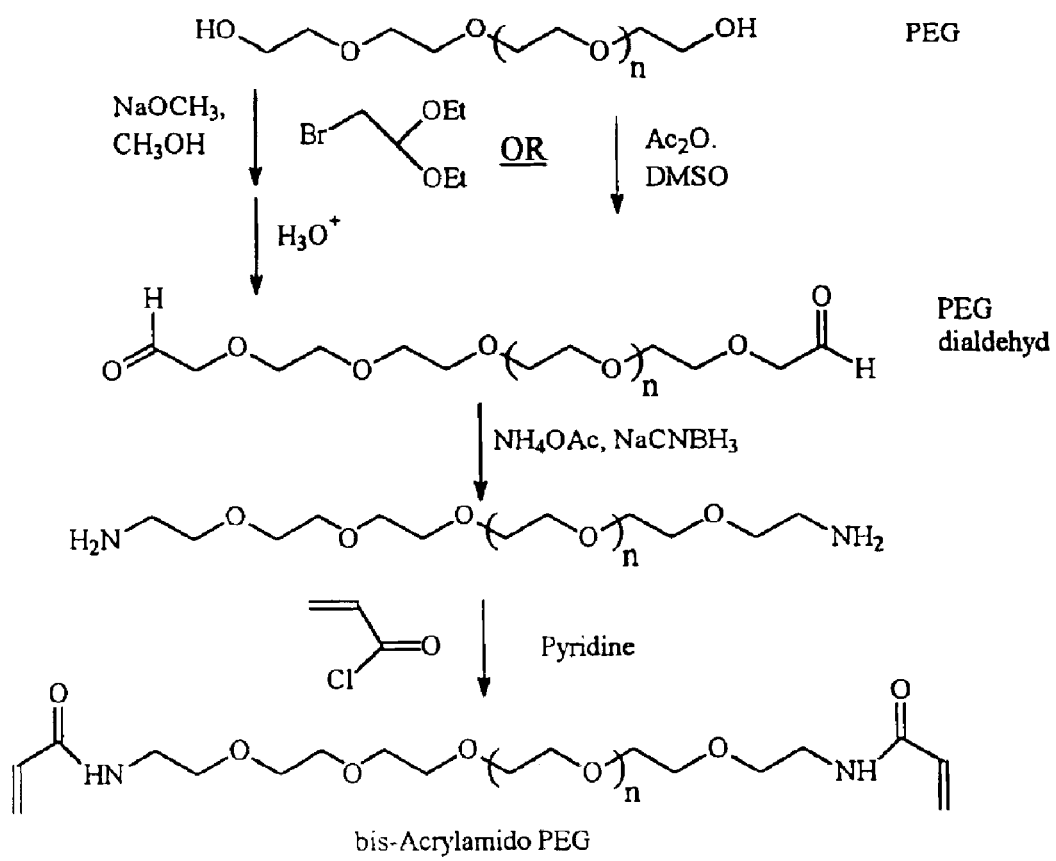
FIG. 8. Shows a synthetic pathway for preparing bis-acrylamido polyethylene glycol crosslinkers from polyethylene glycols of any length.
Figure 9:
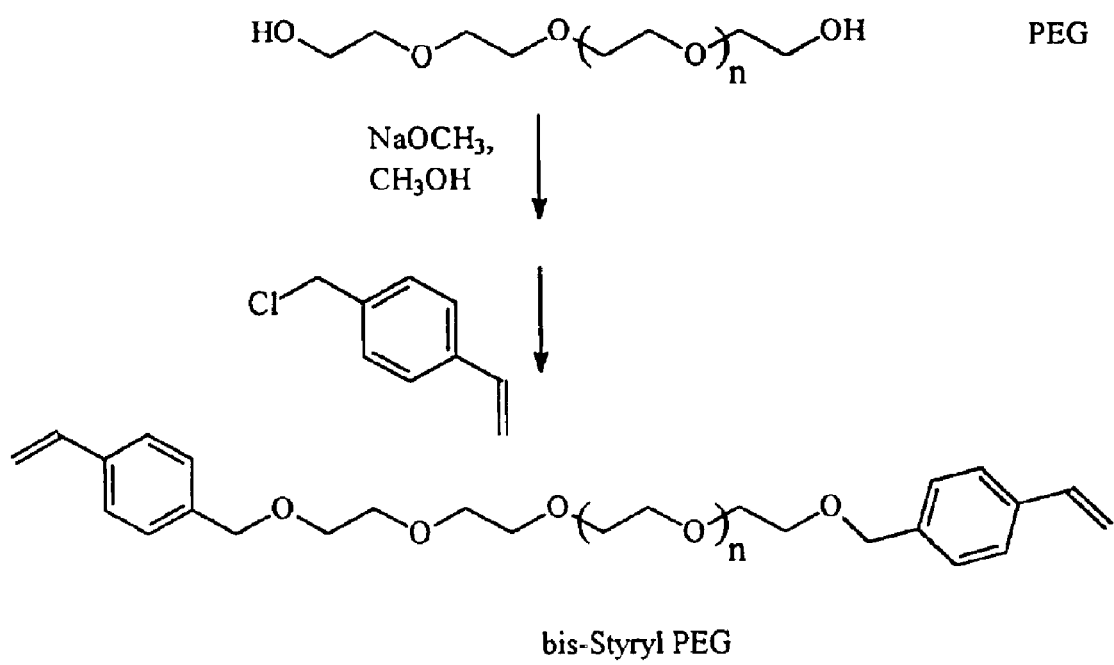
FIG. 9. Shows a method for synthesis of bis-styryl polyethylene glycol crosslinkers from polyethyelene glycols of any length.

Preparation of Polyacrylic Acid Composite Columns from 200 Micron Polybutadiene-Sand: Comparison of Results With and Without Bis-acrylamido PEG Crosslinker The polybutadiene sand, prepared by the method of Example 22, was packed into 4.6×100 mm HPLC columns with a slurry packing apparatus. A solution of acrylic acid (0.15 molar), 2,2'-azobis (2-methylpropioniamidine) dihydrochloride (0.0015 molar) was prepared in water and degassed by bubbling nitrogen into it for 30 minutes. This solution was injected into one of the columns and the ends were plugged. A second solution with the same concentrations of acrylic acid and the azo initiator was prepared, and bis-acrylamido PEG 1900, prepared by the method of Example 4, was added to a concentration of 0.003 molar. This was injected into the a second column packed with polybutadiene-coated sand and the ends were plugged. The two columns were heated in a 61 degree water bath for 17 hours. The columns plumbed into an HPLC and were flushed out with repeated cycles of 1.0 M nitric acid, water, 0.1 M ammonia, and water. Copper sulfate (0.01 molar) was pumped into the column and the effluent of the column was monitored by a UV-visible detector set at 799 nm. After the columns reached saturation with copper, as shown by the concentration of copper in the effluent rising to the same level as the influent, the columns were rinsed with water until the absorbance at 799 nm returned to baseline. Nitric acid, 1.0 molar, was pumped into the column to protonate the interstitial polymer network of polyacrylic acid, and the copper eluted as a detectable peak. The top panel of FIG. 5 is the chromatogram measured with the column that had no bis-acrylamido PEG crosslinker and shows a very small copper elution peak at 6.5 minutes. The capacity of this column was very low and less than 0.01 moles of carboxylate per mL of interstitial void volume. The lower panel of FIG. 5 shows the chromatogram for the column with the bis-acrylamido PEG crosslinker. The large copper elution peak at 14.5 minutes shows the high capacity of this IPN. Based upon an interstitial void volume of 44 percent of the total volume, the capacity of the column is calculated to be 0.15 moles carboxylate per liter of void volume. This capacity corresponds to a near quantitative yield of polyacrylic acid grafted in the interstitial spaces. After measuring the copper capacities of the respective columns, one of the end fittings was removed and the material inside was extruded from the columns by pumping water into the columns. In the case of the column with crosslinker, the sand extruded as a cohesive mass. For the column with no crosslinker, the sand particles did not adhere together. The pellet in the bottom of FIG. 6 shows is a portion of the extruded composite. The cylinder in the top of FIG. 6 is a scan of an interstitial composite that was extruded from a column made with 11 micron microspheres, acrylic acid, and the bis-acrylamido PEG crosslinker.

Example 24

Preparation of a Capillary Column with an Epoxide Activated IPN with Polyglycidyl Methacrylate A glass capillary column (40 microns internal diameter) was reacted with the trichlorosilyl PEG, prepared by the method of Example 1, by injecting the toluene solution into the column, plugging the ends, and permitting the silanization reaction to proceed overnight. The end plugs were removed and the column was flushed out with toluene and then methanol. A solution of 0.006 molar radical initiator, AIBN, was prepared in 30 mL glycidyl methacrylate. Bis-acrylamido PEG 1900, prepared by the method of Example 4, was added until the solution was saturated in the crosslinker (approximately a 25% w/w solution). Approximately 200 mg of basic alumina was added to adsorb the inhibitor, and the suspension was agitated and degassed for 45 minutes by bubbling nitrogen into it. The suspension was allowed to settle for 5 minutes, and the supernatant initiator, monomer and crosslinker solution was withdrawn with a syringe and injected into the capillary column. The inlet and outlet of the column were plugged. The cartridge was immersed in a 71 degree Centigrade water bath for 20 minutes to perform the graft polymerization reaction. The reaction was terminated by removing the unit from the bath and flushing it with acetone.

Example 25

Figure 10:
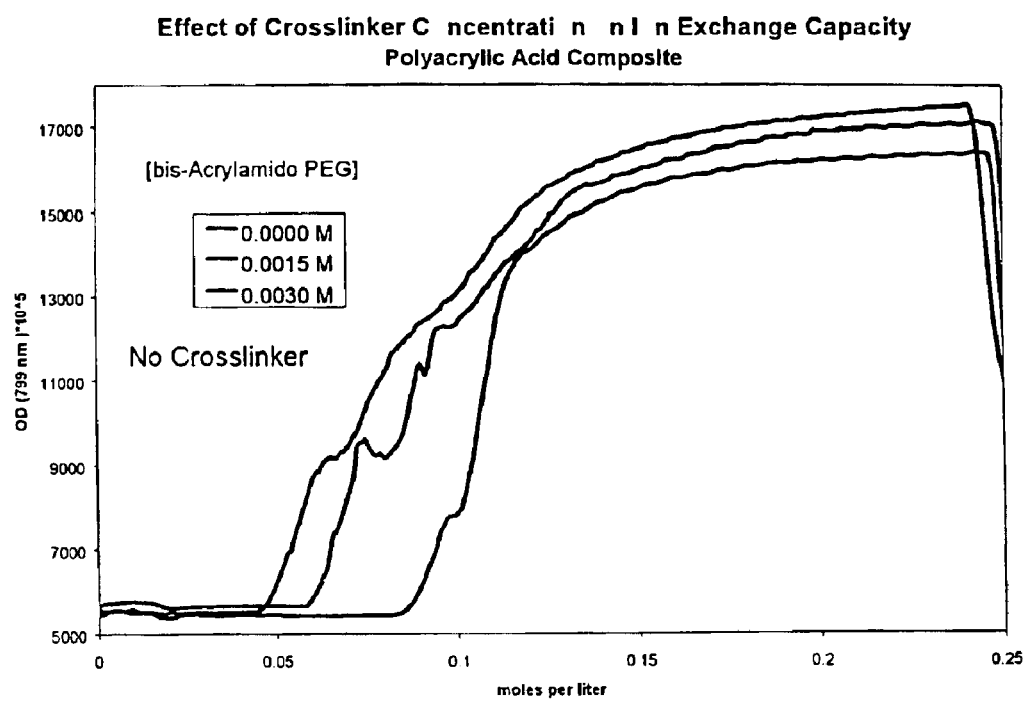
FIG. 10. The graphs show the copper adsorption isotherms for the composite columns made with polyacrylic acid, using 0, 1, and 2 molar percent of bis-acrylamido PEG crosslinker. The 2 mole percent crosslinker uptake curve has the longest retention time. The shortest retention time curve, corresponding to the lowest capacity, curve was measured for the experiment with no crosslinker.
Figure 11:
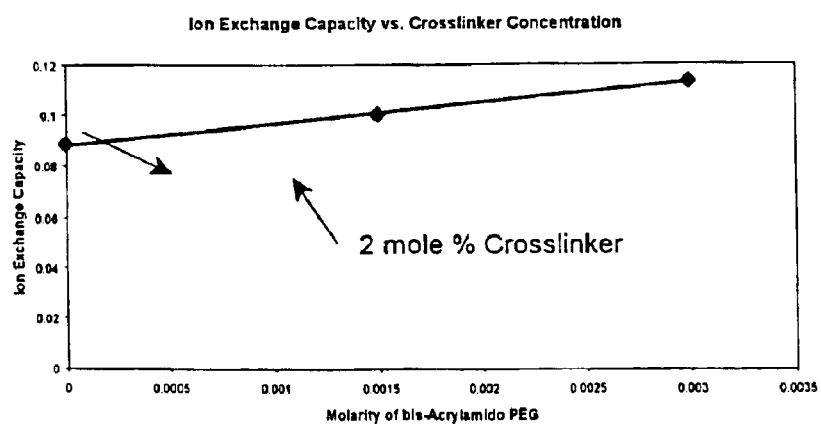
FIG. 11. Shows a graph of the ion exchange capacity of the polyacrylic acid IPN columns prepared in Example 25 as a function of the mole percent of crosslinker used.
Figure 12:
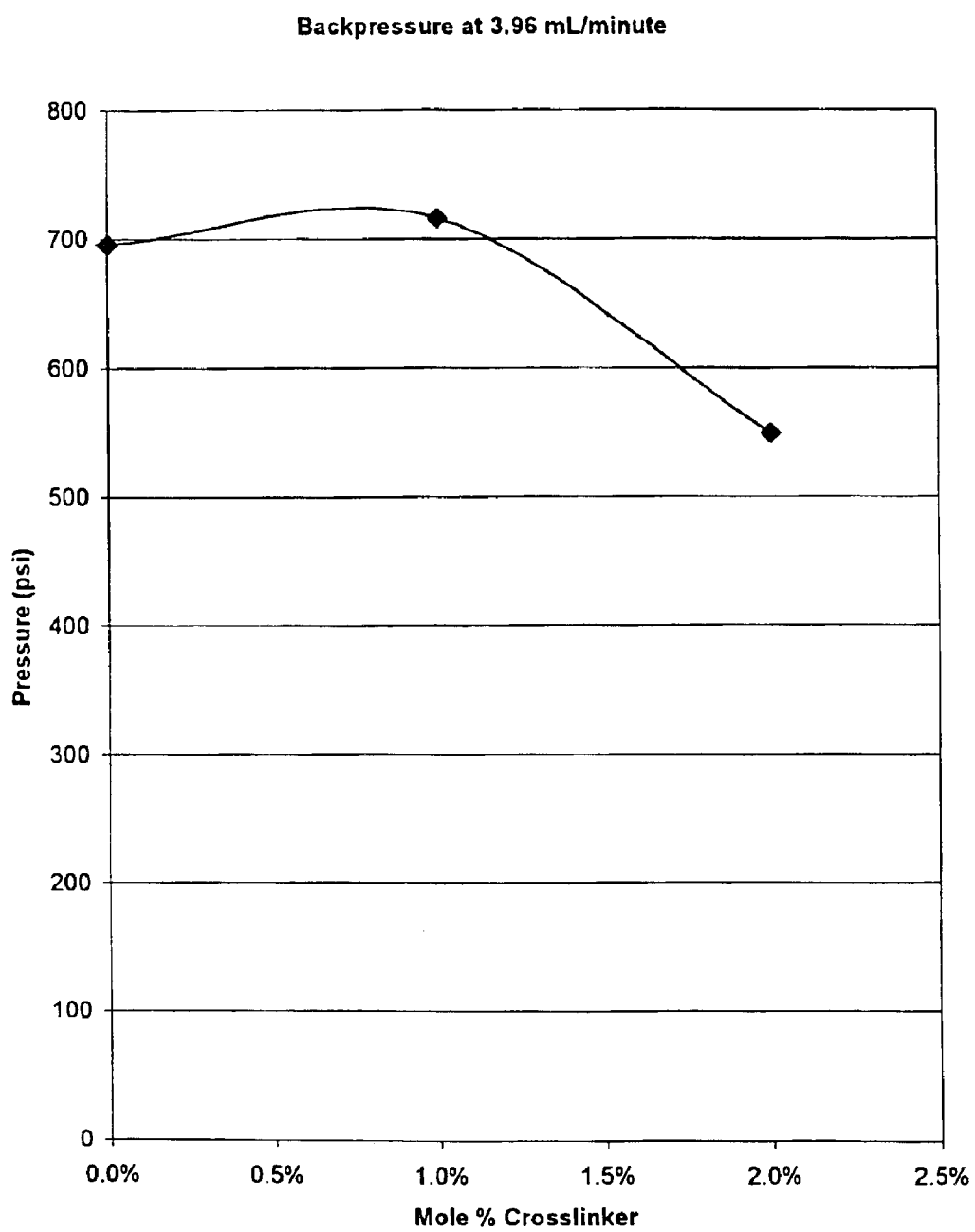
FIG. 12. The back pressures of the columns, prepared in Example 25 at 3.96 mL/minute flow rate are graphed. The graph shows that the back pressure decreases with increasing amount of crosslinker, despite the fact that the higher capacity and the mass of the IPN of the 2% crosslinker column is considerably higher than with the other columns.

Preparation of a Composite Matrix by Polymerization of 0.15 Molar Acrylic Acid, Using Various Amounts of bis-Acrylamido PEG Crosslinker The 11 micron polyethylene glycol-modified silica prepared in Example 3 was pressure packed with water into 4.6×33 mm HPLC columns by standard methods used for packing high performance columns. The column ends were fitted with end fittings and frits. A 0.0015 molar solution of the radical initiator, 2,2'-azobis (2-methylpropioniamidine) dihydrochloride and 0.15 molar acrylic acid was prepared in degassed water. Bis-acrylamido PEG 1900, prepared by the method of Example 4, was added to portions of the solutions, so that the concentrations of the bis-crosslinker were respectively 0, 1, and 2 molar percent relative to the acrylic acid. The polymerization solutions were injected into columns with a syringe equipped with a HPLC column adaptor (Upchurch Scientific) and then the ends of the columns were plugged. The columns were immersed in a 61 degree water bath for 21 hours to perform the graft polymerization reaction. The reactions were terminated by removing the column from the bath and flushing it with water, using an HPLC pump. The capacities of the three columns were measured by copper titration isotherms, shown in FIG. 10. A graph of the ion exchange capacity of the polyacrylic acid IPN columns, as a function of the mole percent of crosslinker used, is shown in FIG. 11. The back pressures of the columns at 3.96 mL/minute flow rate are graphed in FIG. 12. The graph shows that the back pressure decreases with increasing amount of crosslinker, despite the fact that the higher capacity of the 2% crosslinker column is considerably higher than with the other columns.

Example 26

Preparation of a Composite Matrix by Polymerization of 0.6 Molar Glycidyl Methacrylate The 11 micron polyethylene glycol-modified silica prepared in Example 3 was pressure packed with water into 4.6×33 mm HPLC columns by standard methods used for packing high performance columns. The column ends were fitted with end fittings and frits. The columns were rinsed out with 3 mL of tet-butyl alcohol. A 0.0059 molar solution of the radical initiator, AIBN, and 0.57 molar glycidyl methacrylate was prepared in degassed tert-butyl alcohol. Bis-acrylamido PEG 1900, prepared by the method of Example 4, was added to the solution, so that the concentration of the bis-crosslinker were respectively 2.3 mole percent relative to the glycidyl methacrylate. The polymerization solution was injected into column with a syringe equipped with a HPLC column adaptor (Upchurch Scientific) and then the ends of the columns were plugged. The columns were immersed in a 61 degree water bath for 21 hours to perform the graft polymerization reaction. The reactions were terminated by removing the column from the bath and flushing it with tetrahydrofuran, using an HPLC pump. A 1.0 molar solution of ethylene diamine in methanol was injected into the column and allowed to react for two hours. The column was flushed out with water, and the capacity of the columns was measured by copper titration isotherms, similar to that shown in FIG. 10. The interstitial concentration of amine nitrogen atoms was 0.27 moles of amine nitrogen atoms per liter of interstitial volume.

What is claimed is:

1. A matrix comprising solid particles and interstitial space comprising (a) a cross-linked interstitial polymer network covalently attached to said particles which forms an integrated contiguous network in said interstitial space that is permeable to liquids is effectively a large pore polymer contained within the interstitial space of the matrix and is sufficiently thin or dilute so as to not act as a significant barrier to fluid flow, and (b) a member of a binding pair, wherein at least one of the monomers used to synthesize said network comprises a hydrophilic monomer.

2. The matrix of claim 1 wherein said interstitial polymer network further comprises a tether molecule that covalently links said interstitial polymer network to said particles.

3. The matrix of claim 1 wherein said solid support further comprises a blocking reagent.

4. The matrix of claim 1 wherein said solid particles comprise metal, metal oxide, resin or glass.

5. The matrix of claim 1 wherein said solid particles comprise silica.

6. The matrix of claim 1 wherein said member of said binding pair is a cationic or anionic moiety.

7. The matrix of claim 1 wherein said cross-linked interstitial polymer network comprises pores comprising at least one dimension of at least 100 nanometers.

8. The matrix of claim 1 wherein said cross-linked interstitial polymer network comprises pores comprising at least one dimension of at least 500 nanometers.

9. A matrix comprising solid particle and interstitial space comprising (a) a cross-linked interstitial polymer network covalently attached to said particles which forms an integrated contiguous network in said interstitial space that is permeable to liquids is effectively a large pore polymer contained within the interstitial space of the matrix and is sufficiently thin or dilute so as to not act as a significant barrier to fluid flow, and (b) a reactive moiety, wherein at least one of the monomers use to synthesize said polymer network comprises a hydrophilic monomer.

10. The matrix of claim 9 wherein said reactive moiety comprises a chemical catalyst, an enzyme or a chemical reagent.

11. The matrix of claim 9 wherein said cross-linked interstitial polymer network comprises pores comprising at least one dimension of at least 100 nanometers.

12. The matrix of claim 9 wherein said cross-linked interstitial polymer network comprises pores comprising at least one dimension of at least 500 nanometers.

* * * * *